(12) United States Patent
Busch et al.

(10) Patent No.: US 12,653,725 B2
(45) Date of Patent: *Jun. 16, 2026

(54) ABSORBENT ARTICLES AND METHODS OF MAKING THE SAME

(71) Applicant: The Procter & Gamble Company, Cincinnati, OH (US)

(72) Inventors: James William Busch, Maineville, OH (US); Michael Dale Trennepohl, Cincinnati, OH (US); Steven Joseph Waas, Mason, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 617 days.

This patent is subject to a terminal disclaimer.

(21) Appl. No.: 18/096,079

(22) Filed: Jan. 12, 2023

(65) Prior Publication Data

US 2023/0165726 A1     Jun. 1, 2023

Related U.S. Application Data

(63) Continuation of application No. 16/381,075, filed on Apr. 11, 2019, now Pat. No. 11,576,824.

(Continued)

(51) Int. Cl.
*A61F 13/15* (2006.01)
*B32B 38/00* (2006.01)

(52) U.S. Cl.
CPC .. *A61F 13/15699* (2013.01); *A61F 13/15585* (2013.01); *A61F 13/15617* (2013.01);
(Continued)

(58) Field of Classification Search
CPC .......... A61F 13/15699; A61F 13/15585; A61F 13/15617; A61F 13/15756;
(Continued)

(56) References Cited

U.S. PATENT DOCUMENTS

| | | | |
|---|---|---|---|
| 1,946,626 | A | 2/1934 | Jurgensen |
| 2,296,341 | A | 9/1942 | Fourness |

(Continued)

FOREIGN PATENT DOCUMENTS

| | | | |
|---|---|---|---|
| EP | 0203821 | A2 | 12/1986 |
| EP | 0631768 | A1 | 1/1995 |

(Continued)

OTHER PUBLICATIONS

Search Report and Written Opinion for PCT/US2019/026971 dated Jun. 25, 2019.

(Continued)

*Primary Examiner* — George R Koch
*Assistant Examiner* — Christopher C Caillouet
(74) *Attorney, Agent, or Firm* — Sarah M. DeCristofaro

(57) ABSTRACT

Methods of making disposable absorbent articles are herein. The method includes the steps: obtaining a carrier web; obtaining first absorbent core web and a second absorbent core web; cutting the first absorbent core web in a nesting configuration thereby forming a plurality of discrete first absorbent cores; cutting the second absorbent core web in a nesting configuration thereby forming a plurality of discrete second absorbent cores; joining a discrete second absorbent core to a discrete first absorbent core and to the carrier web, thereby forming a laminate structure web, wherein a leading edge of the discrete first absorbent core is spaced from a leading edge of the discrete second absorbent core in the machine direction; joining a backsheet web to the laminate structure web thereby forming an absorbent article web; and cutting the absorbent article web into a plurality of discrete absorbent articles.

8 Claims, 14 Drawing Sheets

Related U.S. Application Data

(60) Provisional application No. 62/655,951, filed on Apr. 11, 2018.

(52) U.S. Cl.
CPC ... *A61F 13/15756* (2013.01); *A61F 13/15764* (2013.01); *B32B 38/0004* (2013.01); *Y10T 156/1062* (2015.01); *Y10T 156/1075* (2015.01)

(58) Field of Classification Search
CPC ........ A61F 13/15764; A61F 2013/5355; A61F 13/535; Y10T 156/1087; Y10T 156/1062; Y10T 156/1075; B32B 38/0004
See application file for complete search history.

(56) References Cited

U.S. PATENT DOCUMENTS

| | | | |
|---|---|---|---|
| 3,156,242 A | 11/1964 | Crowe, Jr. | |
| 3,386,442 A | 6/1968 | Reinhardt | |
| 3,406,688 A | 10/1968 | Cubitt | |
| 3,431,911 A | 3/1969 | Meisel, Jr. | |
| 3,512,530 A | 5/1970 | Jones, Sr. | |
| 3,528,421 A | 9/1970 | Vaillancourt | |
| 3,572,342 A | 3/1971 | Lindquist | |
| 3,604,422 A | 9/1971 | Sabee | |
| 3,651,809 A | 3/1972 | Champaigne, Jr. | |
| 3,695,269 A | 10/1972 | Malaney | |
| 3,799,167 A | 3/1974 | Miller et al. | |
| 3,805,790 A | 4/1974 | Kaczmarzyk | |
| 3,815,602 A | 6/1974 | Johns et al. | |
| 3,825,006 A | 7/1974 | Ralph | |
| 3,838,693 A | 10/1974 | Sherman | |
| 3,871,037 A | 3/1975 | Willington | |
| 3,878,283 A | 4/1975 | Jones, Sr. | |
| 3,881,489 A | 5/1975 | Hartwell | |
| 3,929,135 A | 12/1975 | Thompson | |
| 3,954,721 A | 5/1976 | Gross | |
| 3,978,185 A | 8/1976 | Buntin et al. | |
| 3,983,095 A | 9/1976 | Bashaw et al. | |
| 3,989,867 A | 11/1976 | Sisson | |
| 3,996,936 A | 12/1976 | Widlund et al. | |
| 4,047,531 A | 9/1977 | Karami | |
| 4,102,340 A | 7/1978 | Mesek et al. | |
| 4,136,697 A | 1/1979 | Smith | |
| 4,211,227 A | 7/1980 | Anderson et al. | |
| 4,231,357 A | 11/1980 | Hessner | |
| 4,269,188 A | 5/1981 | Nishizawa et al. | |
| 4,285,342 A | 8/1981 | Mesek | |
| 4,324,246 A | 4/1982 | Mullane et al. | |
| 4,333,464 A | 6/1982 | Nakano | |
| 4,333,465 A | 6/1982 | Wiegner | |
| 4,335,722 A | 6/1982 | Jackson | |
| 4,338,371 A | 7/1982 | Dawn et al. | |
| 4,341,216 A | 7/1982 | Obenour | |
| 4,342,314 A | 8/1982 | Radel et al. | |
| 4,354,901 A | 10/1982 | Kopolow | |
| 4,364,787 A * | 12/1982 | Radzins | A61F 13/15593 156/578 |
| 4,364,992 A | 12/1982 | Jto et al. | |
| 4,381,783 A | 5/1983 | Elias | |
| 4,397,644 A | 8/1983 | Matthews et al. | |
| 4,410,324 A | 10/1983 | Sabee | |
| 4,411,660 A | 10/1983 | Dawn et al. | |
| 4,463,045 A | 7/1984 | Ahr | |
| 4,480,000 A | 10/1984 | Hirt et al. | |
| 4,500,315 A | 2/1985 | Iskra | |
| 4,536,181 A | 8/1985 | Cook | |
| 4,537,590 A | 8/1985 | Iskra | |
| 4,557,777 A | 12/1985 | Sabee | |
| 4,560,372 A | 12/1985 | Pieniak | |
| 4,560,379 A | 12/1985 | Stemmler | |
| 4,591,523 A | 5/1986 | Thompson | |
| 4,609,518 A | 9/1986 | Curro et al. | |
| 4,610,678 A | 9/1986 | Weisman | |
| 4,629,643 A | 12/1986 | Curro | |
| 4,655,757 A | 4/1987 | Mcfarland | |
| 4,666,439 A | 5/1987 | Williams | |
| 4,673,402 A | 6/1987 | VVeisman et al. | |
| 4,676,784 A | 6/1987 | Erdman | |
| 4,685,914 A | 8/1987 | Holtman | |
| 4,695,278 A | 9/1987 | Lawson | |
| 4,699,823 A | 10/1987 | Kellenberger | |
| 4,704,115 A | 11/1987 | Buell | |
| 4,710,187 A | 12/1987 | Boland | |
| 4,713,068 A | 12/1987 | Wang et al. | |
| 4,762,521 A | 8/1988 | Roessler et al. | |
| 4,770,656 A | 9/1988 | Proxmire | |
| 4,781,711 A | 11/1988 | Houghton et al. | |
| 4,790,839 A | 12/1988 | Ahr | |
| 4,795,454 A | 1/1989 | Dragoo | |
| 4,798,603 A | 1/1989 | Meyer | |
| 4,806,408 A | 2/1989 | Pierre et al. | |
| 4,818,600 A | 4/1989 | Braun et al. | |
| 4,834,735 A | 5/1989 | Alemany et al. | |
| 4,888,093 A | 12/1989 | Dean | |
| 4,888,231 A | 12/1989 | Angstadt | |
| 4,888,238 A | 12/1989 | Katz | |
| 4,900,318 A | 2/1990 | Toth | |
| 4,909,803 A | 3/1990 | Aziz | |
| 4,911,700 A | 3/1990 | Makoui | |
| 4,923,454 A | 5/1990 | Seymour | |
| 4,935,022 A | 6/1990 | Lash | |
| 4,944,735 A | 7/1990 | Mokry | |
| 4,950,264 A | 8/1990 | Osborn, III | |
| 4,973,325 A | 11/1990 | Sherrod et al. | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,009,650 A | 4/1991 | Bernardin | |
| 5,013,309 A * | 5/1991 | Baigas, Jr. | A61F 5/4401 604/385.21 |
| 5,037,409 A | 8/1991 | Wisneski | |
| 5,061,259 A | 10/1991 | Goldman | |
| 5,061,260 A | 10/1991 | Callahan | |
| 5,069,676 A | 12/1991 | Ito | |
| 5,079,004 A | 1/1992 | Blank | |
| 5,087,506 A | 2/1992 | Palumbo | |
| 5,098,422 A | 3/1992 | Davis | |
| 5,134,007 A | 7/1992 | Mesek et al. | |
| 5,147,343 A | 9/1992 | Kellenberger | |
| 5,147,345 A | 9/1992 | Lavon | |
| 5,149,335 A | 9/1992 | Kellenberger | |
| 5,176,668 A | 1/1993 | Bernardin | |
| 5,192,606 A | 3/1993 | Proxmire | |
| 5,234,423 A | 8/1993 | Alemany et al. | |
| 5,294,478 A | 3/1994 | Wanek et al. | |
| 5,300,053 A | 4/1994 | Genaro | |
| 5,300,054 A | 4/1994 | Feist | |
| 5,304,161 A | 4/1994 | Noel et al. | |
| 5,387,207 A | 2/1995 | Dyer | |
| 5,411,497 A | 5/1995 | Tanzer | |
| 5,425,725 A | 6/1995 | Tanzer | |
| 5,433,715 A | 7/1995 | Tanzer | |
| 5,440,061 A | 8/1995 | Gibson | |
| 5,454,800 A | 10/1995 | Hirt et al. | |
| 5,466,513 A | 11/1995 | Wanek | |
| 5,509,915 A | 4/1996 | Hanson | |
| 5,599,335 A | 2/1997 | Goldman | |
| 5,628,097 A | 5/1997 | Benson | |
| 5,665,452 A | 9/1997 | Langdon et al. | |
| 5,762,844 A | 6/1998 | Van Himbergen et al. | |
| 5,792,404 A | 8/1998 | Cree et al. | |
| 5,830,202 A | 11/1998 | Bogdanski et al. | |
| 5,853,402 A | 12/1998 | Faulks | |
| 5,885,265 A | 3/1999 | Osborn, III et al. | |
| 6,025,535 A | 2/2000 | Octavio et al. | |
| 6,068,620 A | 5/2000 | Chmielewski et al. | |
| 6,183,587 B1 | 2/2001 | Mcfall et al. | |
| 6,436,508 B1 | 8/2002 | Ciammaichella et al. | |
| 6,623,464 B2 | 9/2003 | Bewick-sonntag | |
| 6,664,439 B1 | 12/2003 | Arndt et al. | |
| 7,172,801 B2 | 2/2007 | Hoying et al. | |

(56) References Cited

U.S. PATENT DOCUMENTS

| | | | |
|---|---|---|---|
| 7,402,723 B2 | 7/2008 | Stone et al. | |
| 7,410,683 B2 | 8/2008 | Curro et al. | |
| 7,553,532 B2 | 6/2009 | Turner et al. | |
| 7,648,752 B2 | 1/2010 | Hoying et al. | |
| 7,655,176 B2 | 2/2010 | Stone et al. | |
| 7,744,713 B2 | 6/2010 | Blessing et al. | |
| 7,785,690 B2 | 8/2010 | Turner et al. | |
| 7,838,099 B2 | 11/2010 | Curro et al. | |
| 7,838,722 B2 | 11/2010 | Blessing et al. | |
| 8,105,301 B2 | 1/2012 | Baer et al. | |
| 8,180,603 B2 | 5/2012 | Blessing et al. | |
| 8,206,533 B2 | 6/2012 | Hundorf et al. | |
| 8,440,286 B2 | 5/2013 | Curro et al. | |
| 8,552,251 B2 | 10/2013 | Zhou et al. | |
| 8,568,566 B2 | 10/2013 | Jackels et al. | |
| 8,603,622 B2 | 12/2013 | Rottger et al. | |
| 8,614,365 B2 | 12/2013 | Hammons | |
| 8,704,036 B2 | 4/2014 | Hammons et al. | |
| 8,728,049 B2 | 5/2014 | Hammons et al. | |
| 8,839,836 B2 * | 9/2014 | Cocozzella | A61F 13/15 |
| | | | 156/263 |
| 9,238,089 B2 | 1/2016 | Chmielewski et al. | |
| 9,999,550 B2 | 6/2018 | Piantoni et al. | |
| 10,471,620 B2 | 11/2019 | Bittner | |
| 11,129,755 B2 | 9/2021 | Hardie et al. | |
| 11,576,824 B2 * | 2/2023 | Busch | A61F 13/535 |
| 2003/0225384 A1 | 12/2003 | Zenker et al. | |
| 2004/0015142 A1 | 1/2004 | Johnston et al. | |
| 2006/0018415 A1 | 1/2006 | Jung | |
| 2006/0069367 A1 | 3/2006 | Widlund et al. | |
| 2008/0312622 A1 | 12/2008 | Hundorf | |
| 2009/0312730 A1 | 12/2009 | Lavon | |
| 2012/0043244 A1 | 2/2012 | Hagner | |
| 2012/0053547 A1 | 3/2012 | Schroeder | |
| 2014/0005623 A1 | 1/2014 | Wirtz et al. | |
| 2014/0163500 A1 | 6/2014 | Roe | |
| 2014/0213997 A1 | 7/2014 | Tsang | |
| 2014/0343523 A1 | 11/2014 | Viens | |
| 2015/0223990 A1 | 8/2015 | Armstrong-ostle et al. | |
| 2015/0351976 A1 | 12/2015 | Viens | |
| 2016/0129661 A1 | 5/2016 | Arora | |
| 2016/0166443 A1 | 6/2016 | Arora et al. | |
| 2016/0167334 A1 | 6/2016 | Arora et al. | |
| 2016/0235602 A1 | 8/2016 | Johns et al. | |
| 2017/0025865 A1 | 1/2017 | Imazaki et al. | |
| 2017/0258647 A1 | 9/2017 | Orr et al. | |
| 2017/0258651 A1 | 9/2017 | Hammons | |
| 2017/0312146 A1 | 11/2017 | Bianchi | |
| 2017/0348166 A1 | 12/2017 | Ebert et al. | |
| 2018/0098890 A1 | 4/2018 | Hardie et al. | |
| 2018/0098891 A1 | 4/2018 | Hardie et al. | |
| 2018/0098893 A1 | 4/2018 | Viens | |
| 2018/0154533 A1 | 6/2018 | Busch et al. | |
| 2019/0314211 A1 | 10/2019 | Busch et al. | |
| 2021/0378882 A1 | 12/2021 | Hardie et al. | |

FOREIGN PATENT DOCUMENTS

| | | |
|---|---|---|
| EP | 0710471 A1 | 5/1996 |
| EP | 0710472 A1 | 5/1996 |
| EP | 0793952 A1 | 9/1997 |
| EP | 1447066 A1 | 8/2004 |
| EP | 2594238 A2 | 5/2013 |
| EP | 2901992 B1 | 12/2016 |
| EP | 3205318 A1 | 8/2017 |
| GB | 1259865 A | 1/1972 |
| GB | 2184389 A | 6/1987 |
| GB | 2184390 A | 6/1987 |
| GB | 2184391 A | 6/1987 |
| WO | 9511652 A1 | 5/1995 |
| WO | 9724097 A1 | 7/1997 |
| WO | 9962801 A2 | 12/1999 |
| WO | 0076447 A1 | 12/2000 |
| WO | 2005060892 A1 | 7/2005 |
| WO | 2012052172 A1 | 4/2012 |
| WO | 2013180937 A1 | 12/2013 |
| WO | 2014145804 A1 | 9/2014 |
| WO | 2015188032 A1 | 12/2015 |

OTHER PUBLICATIONS

Search Report and Written Opinion for PCT/US2019/026905 dated Jun. 25, 2019.

All Office Actions: U.S. Appl. No. 16/381,075, filed Apr. 11, 2019.

Search Report and Written Opinion for PCT/US2019/026934 dated Jun. 25, 2019.

PCT Search Report and Written Opinion for PCT/US2019/026935 dated Jul. 4, 2019.

* cited by examiner

ABSORBENT ARTICLES AND METHODS OF MAKING THE SAME

FIELD OF THE INVENTION

The present invention pertains to disposable absorbent articles suitable for absorbing and containing body exudates.

BACKGROUND OF THE INVENTION

A variety of disposable absorbent articles have been relied on by consumers to handle or manage body exudates. These consumers may include babies, toddlers, children, teenagers, adults, and elderly persons. Thus, it is clear that the types of fluids or body exudates managed by such articles may vary as well to include urine, feces, menses, and other discharges. Typically, in the case of adults, the articles take the form of sanitary napkins, adult incontinence pads, and adult incontinence diapers or undergarments. One of the primary drivers of the desirability of these products to wearers is to give them assurance that when they experience incontinence, the occurrence of such will go unnoticed by others and even more ideally by the wearers.

One way of improving the performance and overall discretion of disposable absorbent articles that has been widely utilized by manufacturers has been the inclusion of superabsorbent polymers which are able to intake increased amounts of liquid and consequently form a swollen hydrogel material. The resulting hydrogel serves to retain fluid such as discharged body liquids within the structure.

While disposable absorbent articles with these superabsorbent materials tend to be highly absorbent and less bulky, there are a number of users of these products that have a high body mass index (BMI) for which these products still leave much to be desired. In particular, these users tend to experience exaggerated bunching of the absorbent article during wear and as a result there can be increased opportunity for leaks to occur.

Consequently, there is a need for a disposable absorbent article which targets to provide increased protection from leakage to consumers which have a high BMI while maintaining a level of discretion to the wearer while in use. And there is a need for a process which facilitates manufacturing of such disposable absorbent articles.

SUMMARY OF THE INVENTION

Described herein are disposable absorbent articles that can provide improved protection from leakage to consumers with a wide variety of BMI's. Additionally, processes disclosed herein can facilitate manufacturing of such articles.

One exemplary process comprises the steps of: obtaining a carrier web and transporting the carrier web in a machine direction; obtaining first absorbent core web and a second absorbent core web; cutting the first absorbent core web in a nesting configuration thereby forming a plurality of discrete first absorbent cores; cutting the second absorbent core web in a nesting configuration thereby forming a plurality of discrete second absorbent cores; joining a discrete second absorbent core to a discrete first absorbent core and to the carrier web, thereby forming a laminate structure web, wherein a leading edge of the discrete first absorbent core is spaced from a leading edge of the discrete second absorbent core in the machine direction; joining a backsheet web to the laminate structure web thereby forming an absorbent article web; and cutting the absorbent article web into a plurality of discrete absorbent articles.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION OF THE INVENTION

Figure 1:
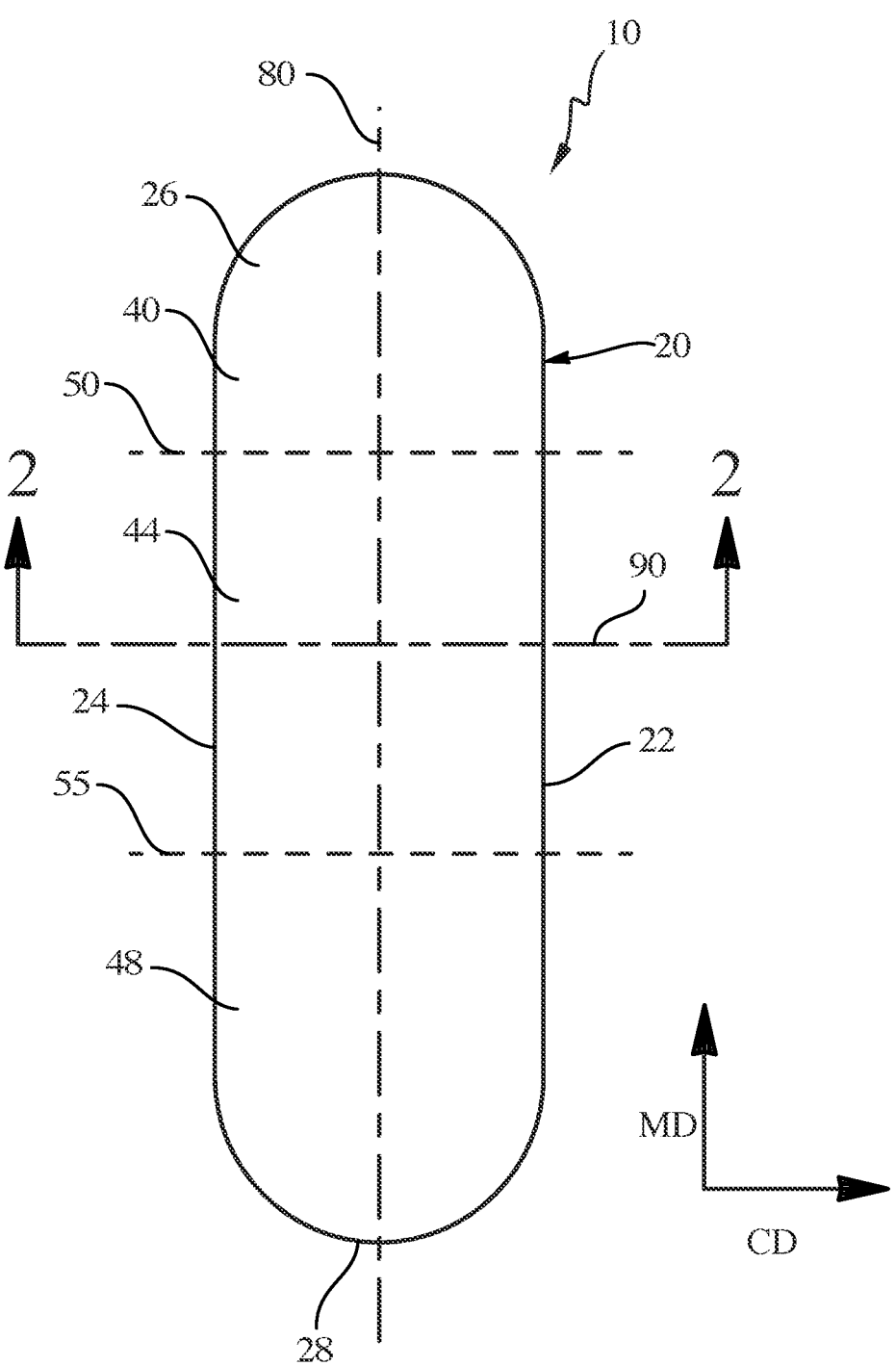
FIG. 1 is a plan view showing an exemplary disposable absorbent article in accordance with the present disclosure.

The following term explanations may be useful in understanding the present disclosure: "The disposable absorbent articles, particularly incontinence pads or pants, of the present invention can provide flexibility to allow for an improved and comfortable fit which is less susceptible to bunching during use. In particular, it is envisioned that the articles of the present invention exhibit heightened structural resiliency from the proposed configuration and orientation of the layers contained therein. For the purposes of this disclosure, reference to an incontinence pad, disposable absorbent article, or absorbent article will be used. However, the present invention may be applied to a plurality of absorbent articles including, but not limited to, sanitary napkins, pantiliners, menstrual pads, diapers, training pants, adult incontinence pants, etc.

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The disposable absorbent articles, particularly incontinence pads or pants, of the present invention can provide flexibility to allow for an improved and comfortable fit which is less susceptible to bunching during use. In particular, it is envisioned that the articles of the present invention exhibit heightened structural resiliency from the proposed configuration and orientation of the layers contained therein. For the purposes of this disclosure, reference to an incontinence pad, disposable absorbent article, or absorbent article will be used. However, the present disclosure may be applied to a plurality of absorbent articles including, but not limited to, sanitary napkins, pantiliners, menstrual pads, diapers, training pants, adult incontinence pants, etc.

There are several factors to consider when designing a disposable absorbent article like an incontinence pad, particularly if improved fit and performance are desired. First, the stiffness of the pad is an important factor. Typically, thinner pads offer less stiffness than their bulkier counterparts. While bulkier pads may be less likely to succumb to the compression that is typical during wear, bulkier pads are less desirable because they can cause the incontinence pad to lose its discreetness during use. Furthermore, some flexibility in the absorbent core can allow the incontinence pad to adjust more readily to the contours of the body of a user during use. Second, the absorbency of the pad is key in determining whether the pad is useful for consumers. Ideally, the pad is well suited to accommodate either small or large loads of exudates. This accommodation means not only storing either type of load sufficiently but also effectively and quickly wicking such loads from a body-contacting surface of the pad such that the user experiences little to no feeling of wetness after the release of the load. In the case of a small load, a wearer should be able to continue to wear the pad for some reasonable time after a release since immediate changing of the pad may not be feasible or desired.

In the past, incontinence pad designs have required a bit of compromise relative to these factors. In contrast, the absorbent articles, which include but are not limited to incontinence, designed pursuant to the present invention account for these factors to arrive at an absorbent article which exhibits improved protection against leakage, particularly for those wearers of a higher than average body mass index (BMI). Namely, incontinence pads of the present disclosure provide good core flexibility, excellent wicking, distribution, and overall absorbency, and in certain embodiments, may include barrier cuffs which stand up during use and contact the wearer in an appropriate location are included as part of the construction to further protect against a likelihood of leakage from the pad.

FIG. 1 shows an absorbent article according to the present disclosure or more particularly an incontinence pad or sanitary napkin 10 (referred to mainly as "incontinence pad" herein) may comprise a longitudinal centerline 80 and a lateral centerline 90. The longitudinal centerline 80 generally extends parallel to the longest dimension of the incontinence pad 10. The lateral centerline 90 extends generally perpendicular to the longitudinal centerline 80 and lies in the same plane as the incontinence pad 10 in a flattened state on a flat surface. The lateral centerline 90 bisects the length of the incontinence pad 10 where the length is parallel to the longitudinal centerline 80, and the longitudinal centerline 80 bisects the width of the incontinence pad 10 where the width is parallel to the lateral centerline 90. Additionally, as shown, the MD direction (machine direction) may be generally parallel to the longitudinal centerline 80 of the incontinence pad 10, and the CD direction (cross-machine direction) may be generally parallel to the lateral centerline 90.

The incontinence pad 10 comprises a generally elongated oval shape. However, any suitable shape may be utilized. Some examples include hourglass (peanut), offset hourglass (one end is wider than an opposite end and a narrowed mid-section between the ends), etc. The incontinence pad 10 may be symmetric about the longitudinal centerline 80 or asymmetric about the longitudinal centerline 80. Similarly, the incontinence pad 10 may be symmetric about the lateral centerline 90 or asymmetric about the lateral centerline 90.

The incontinence pad 10 may further comprise a chassis 20 comprising a plurality of side edges 22 and 24 which extend generally parallel to the longitudinal centerline 80. A pair of end edges 26 and 28 join each of the side edges 22 and 24. One end edge 26 joins the side edges 22 and 24 in the first end region 40 of the incontinence pad 10 while the other end edge 28 joins the side edges 22 and 24 in the second end region 48 of the incontinence pad 10—the second end region 48 being opposite the first end region 40. An intermediate region 44 is disposed between the first end region 40 and the second end region 48.

Incontinence pad 10 may further comprise a first fold line 50 and a second fold line 55. The first fold line 50 can define a boundary between the first end region 40 and the intermediate region 44. The second fold line 55 can define a boundary between the second end region 48 and the intermediate region 44. The first end region 40 can be defined by the end edge 26, the first fold line 50, and a portion of the side edges 22 and 24 disposed between the end edge 26 and the first fold line 50. The intermediate area 44 can be defined by the first fold line 50, the second fold line 55, and a portion of the side edges 22 and 24 disposed between the first fold line 50 and the second fold line 55. The second end region

48 can be defined by the second fold line 55, end edge 28, and a portion of the side edges 22 and 24 disposed between the end edge 28 and the second fold line 55. The fold lines 50 and 55 can be parallel and can be colinear (on average) with the folds which are created via the packaging process for the incontinence pad 10.

Figure 2:
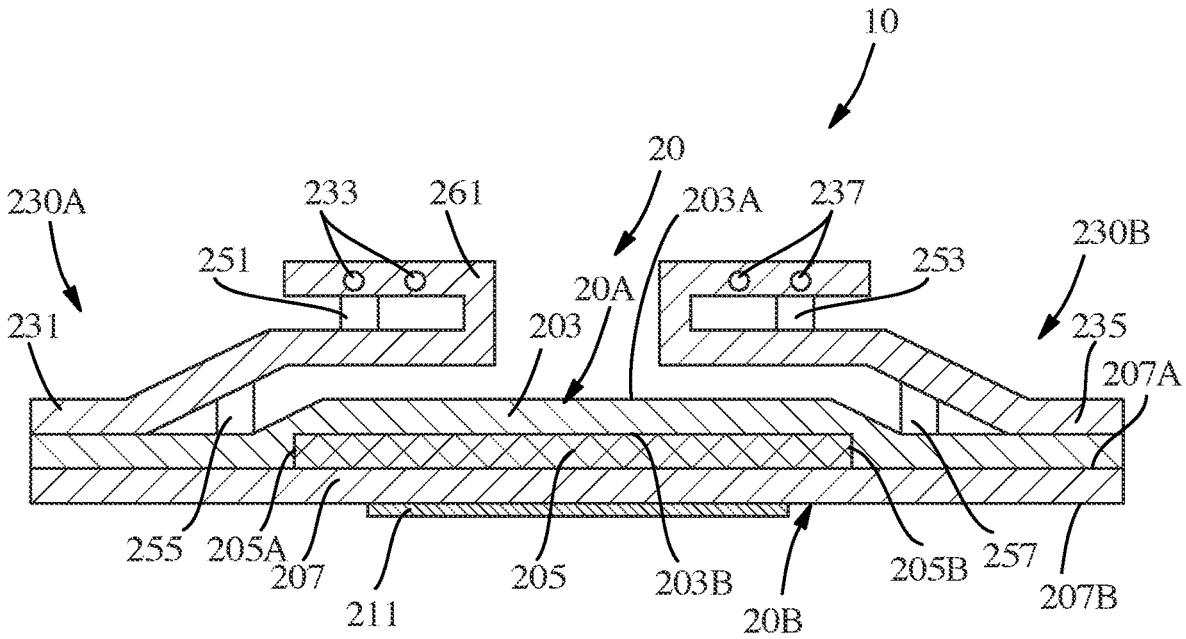
FIG. 2 is a cross-sectional view of the incontinence pad shown in FIG. 1 taken along 2-2.

The chassis 20 of FIG. 1 is shown in cross-section in FIG. 2. Among other things, the chassis 20 comprises a primary topsheet 203. This primary topsheet has a body-facing surface 203A and a garment-facing surface 203B. This chassis 20 of the pad 10 further comprises a backsheet 207 which also comprises its own body-facing surface 207A and opposing garment-facing surface 207B. These two components sandwich an absorbent system 205. In other words, the absorbent system 205 is disposed between the topsheet 203 and the backsheet 207. All three components (i.e., topsheet 203, backsheet 207, and absorbent system 205) form the chassis 20 of the pad 10. Additional layers may very well be included within this chassis 20, particularly between the topsheet 203 and the backsheet 207 but it should be noted that these layers are separate and apart from the absorbent system. Suitable additional layers may include secondary topsheets, acquisition layers, additional distribution layers over and above those which will be discussed below, and other useful layers. In the case of a secondary topsheet, it is disposed beneath the primary topsheet 203 and on the body-facing surface of the core. In some forms, the secondary topsheet (also known as the "STS") has a greater length and/or width than the absorbent system 205.

In some forms, the chassis may further comprise barrier cuffs 230A and 230B. The barrier cuffs are discussed in additional detail hereafter.

The chassis 20 further comprises a wearer-facing surface 20A and a garment-facing surface 20B. The wearer-facing surface 20A may comprise the topsheet 203, and the garment-facing surface 20B may comprise the backsheet 207.

Figure 3:
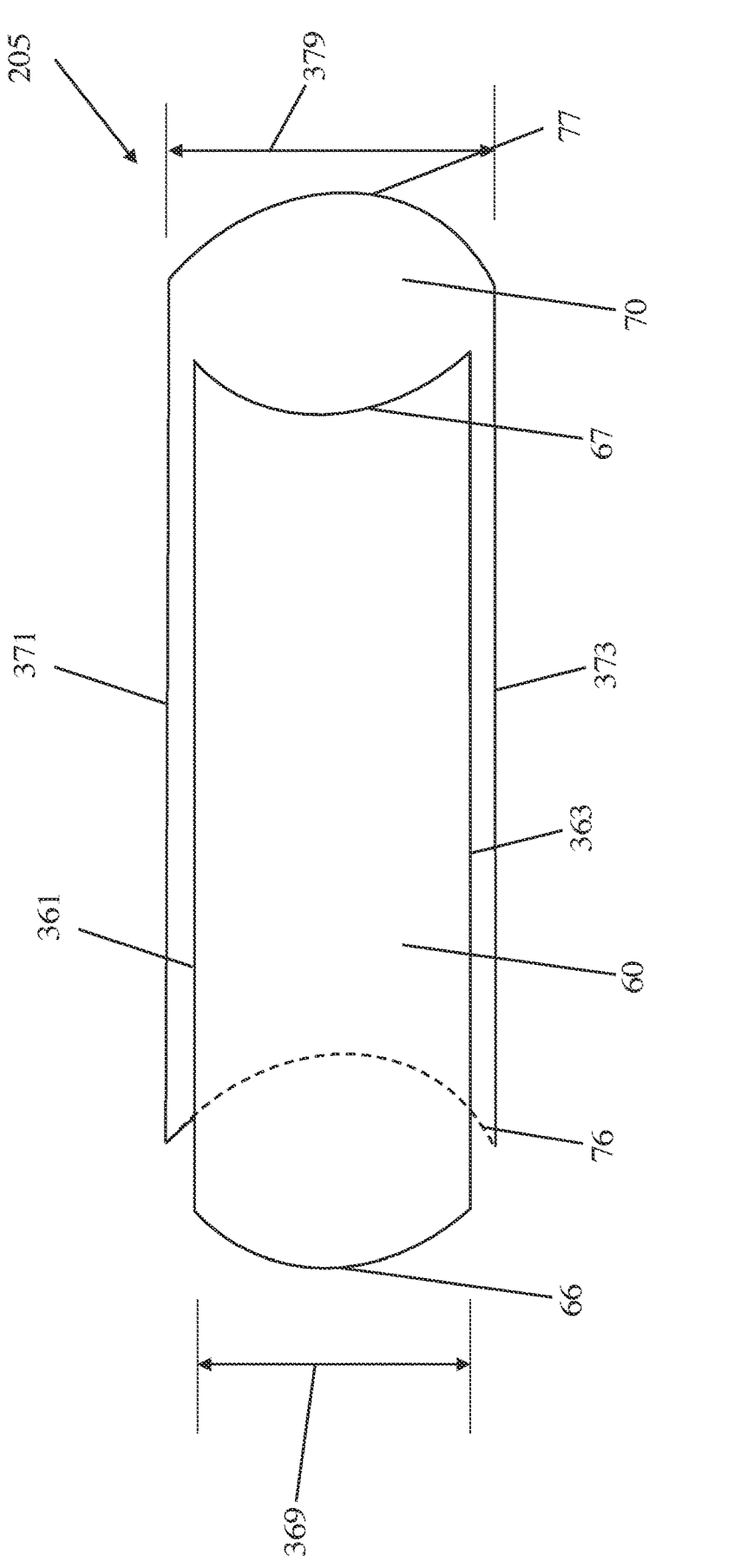
FIG. 3 is a plan view showing an exemplary absorbent system in accordance with the present disclosure.
Figure 4:
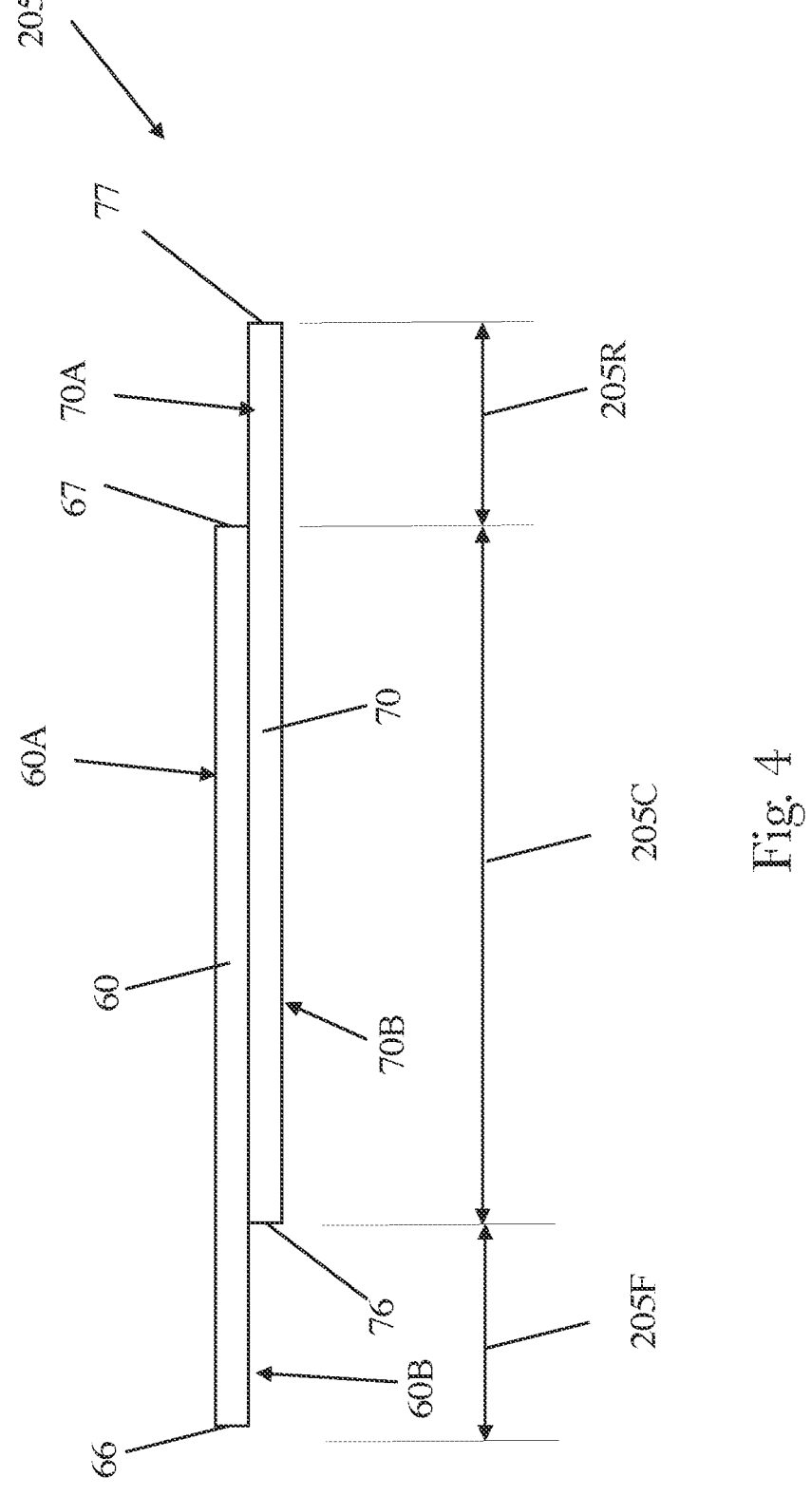
FIG. 4 is an elevation view showing an exemplary absorbent system in accordance with the present disclosure.

The absorbent system 205 is formed from multiple layers and is directed to quickly acquiring the bodily fluid or exudates and distributing them along a length of the core. FIG. 3 depicts the absorbent system of a specific form of the present invention. A plan view of the pad 10 with the primary topsheet 203 and backsheet 207, and any optional layers, removed for facilitated viewing of the absorbent system 205 is provided in FIG. 3. FIG. 4 shows a cross-section of this absorbent system 205 in more detail.

Still referring to FIG. 3, in some forms, the absorbent system 205 may comprise a first absorbent core 60 and a second absorbent core 70. As shown, the first absorbent core 60 has a first leading edge 66 and a first trailing edge 67 which opposes the first leading edge 66. Similarly, the second absorbent core 70 comprises a second leading edge 76 and a second trailing edge 77 opposite the second leading edge 76.

The first absorbent core 60 additionally comprises a first slit edge 361 and a first outer edge 363. Similarly, the second absorbent core 70 comprises a second slit edge 371 and a second outer edge 373. It is worth noting that the first slit edge 361 and the second slit edge 371 are shown on the same side; however, the first slit edge 361 and the second slit edge 371 can be positioned on opposite side of the absorbent system 205 as discussed in additional detail hereafter. Additionally, the first absorbent core 60 has a first width 369 and the second absorbent core 370 comprises a second width 379. As shown, the first width 369 may be less than the second width 379. The respective widths of the first absorbent core layer 60 and the second absorbent core layer 70 are discussed hereafter.

Referring now to FIG. 4, the first absorbent core 60 has an upper surface 60A and a lower surface 60B which opposes the upper surface. Similarly, the second absorbent core 70 has an upper surface 70A and a lower surface 70B. Additionally, in some forms, the first absorbent core 60 and/or the second absorbent core 70 may comprise a laminate structure which includes a plurality of layers, a single layer or a combination of layers. For example, in some forms, the first absorbent core 60 may comprise a laminate structure while the second absorbent core 70 comprises a single layer or vice versa. Such forms are discussed in additional detail hereafter.

As shown, in some forms, the first absorbent core 60 may be joined to the second absorbent core 70 in an offset manner or configuration along the length of the absorbent system 205. As used herein "offset" or "offset manner" means that the layers of interest are staggered and that their respective leading edges or trailing edges are not aligned in a z-direction (i.e., the leading edge of one layer or laminate structure is not coterminous with the trailing edge or leading edge of an adjacent underlying or overlying layer or laminate structure) when the layers or laminate structures overlay one another. This offset joinder of the first and second absorbent cores 60 and 70 results in an overlapping and joined area of the two layers that forms a central portion 205C of the absorbent system 205. The central portion 205C of the absorbent system 205 is consequently bounded on each side by a front end portion 205F and a rear end portion 205R, both of the absorbent system 205. In other words, the front end portion 205F and the rear end 205R portion are respectively disposed at opposing ends of the absorbent system 205. As shown in some forms, a distance between the first leading edge 66 and the second leading edge 76 can define a length of the front end portion 205F. Similarly, a distance between the second trailing edge 77 and the first trailing edge 67 can define a length of the rear end portion 205R. In some forms, the second leading edge 76 may be the leading edge of the absorbent system 205 while the first trailing edge 67 may be the trailing edge of the absorbent system 205.

Figure 5:
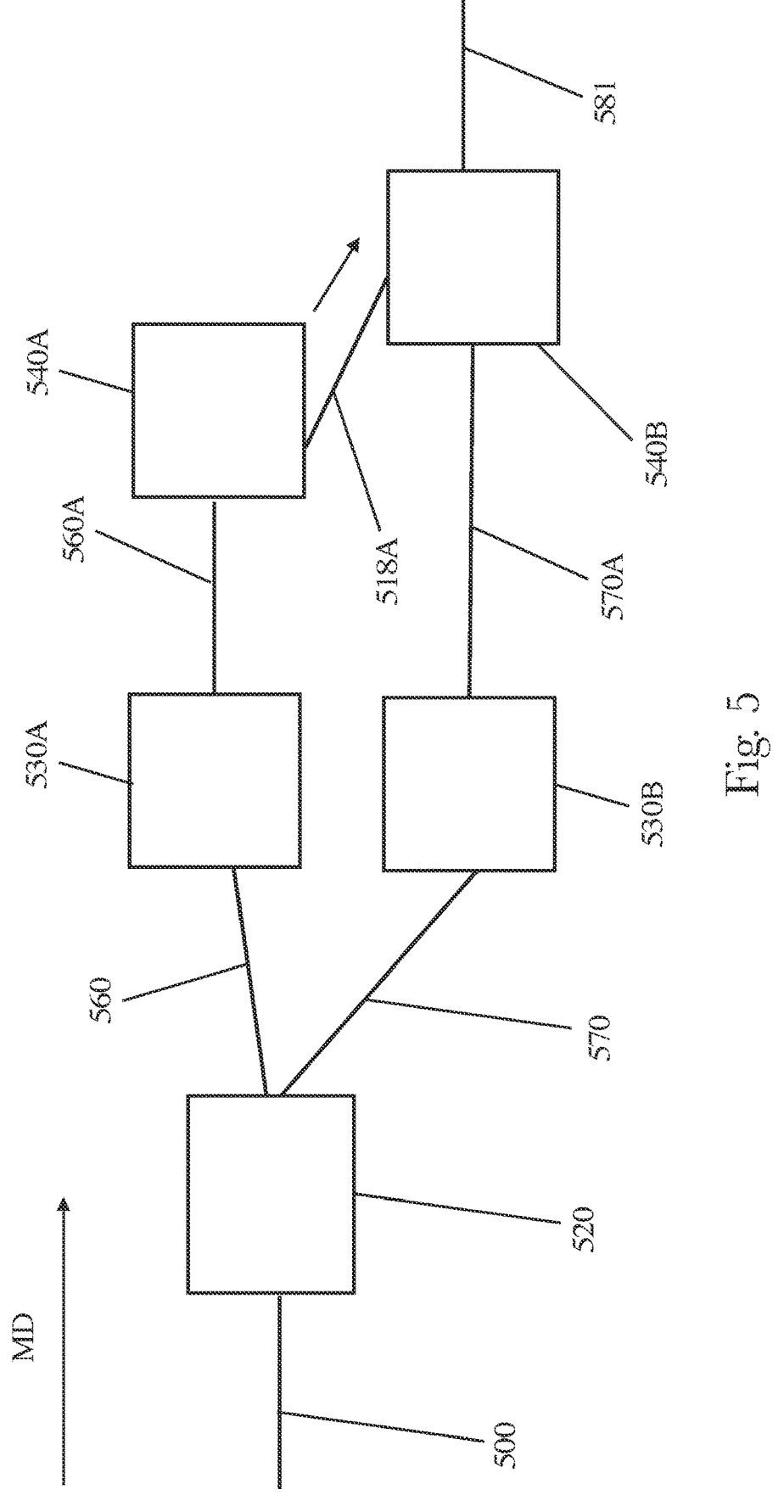
FIG. 5 is a process schematic showing an exemplary process in accordance with the present disclosure.
Figure 6:
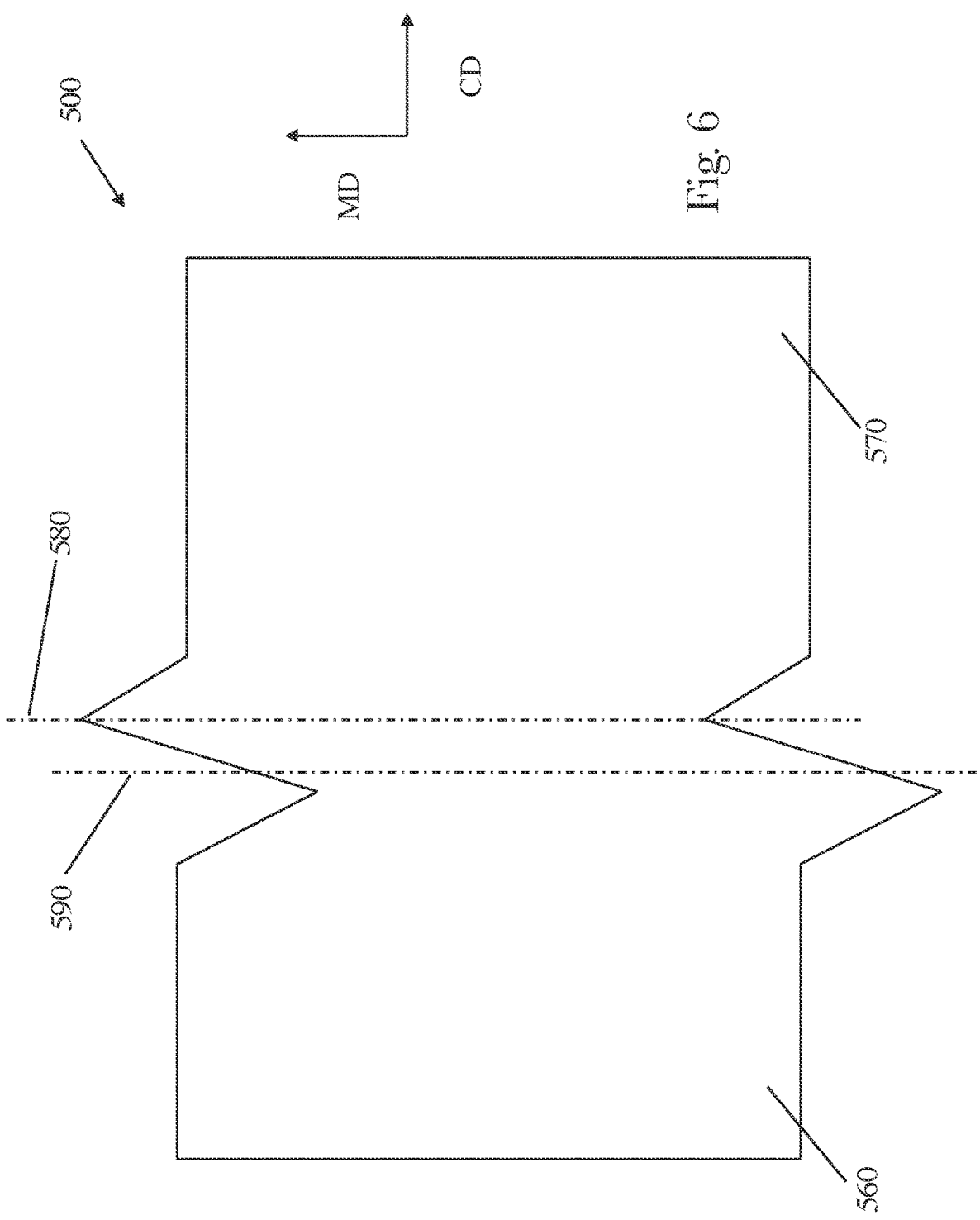
FIG. 6 is a plan view of an absorbent core web in accordance with the present disclosure.

Processing of such forms can be facilitated according to the process of the present disclosure. As shown in FIGS. 5 and 6, an absorbent core web 500 can be obtained from a supplier or can be manufactured by an absorbent article manufacturer or a combination thereof. Additional details of the absorbent core web 500 are provided hereafter. As shown, the absorbent core web 500 can be transported in a machine direction to a slitting machine 520. Slitting machines are well known in the art.

Still referring now to FIGS. 5 and 6, in some forms, the absorbent core web 500 can be slit along a slit line 590 which can be offset from a longitudinal centerline 580 of the absorbent core web 500. In some forms, the slit line 590 may be colinear with the longitudinal centerline 580. As shown, post slitting, two separate webs may be created, namely, a first absorbent core web 560 and a second absorbent core web 570.

It is worth noting that while the slit edge can be created as disclosed herein, it is not necessarily required. Absorbent article manufacturers can obtain the first absorbent core web 560 and/or the second absorbent core web 570 via processing described herein or could receive the first absorbent core web and the second absorbent core web separate. In such instances, the need to slit the absorbent core web would be obviated.

The first absorbent core web 560 may then be provided to a cutting device 530A while the second absorbent core web 570 may be provided to a second cutting device 530B. The first cutting device 530A creates a plurality of discrete first absorbent cores 560A (individually referred to as the first absorbent core 60 shown in FIGS. 3 and 4) from the first absorbent core web 560. The second cutting device 530B creates a plurality of discrete absorbent cores 570A (individually referred to as the second absorbent core 70 shown in FIGS. 3 and 4) from the second absorbent core web 570. Exemplary cutting devices are disclosed in U.S. Patent Application Publication No. 2018/0154533.

Referring now to FIGS. 3-5, as shown, the cutting device 530A can provide the first absorbent core 60 with a convex (male) leading edge 66 while the second cutting device 530B can provide the second absorbent core 70 with a concave (female) leading edge 76. However, forms are contemplated where both the leading edges 66 and 76 are convex (male). Forms are contemplated where both the leading edges are concave (female). Forms are contemplated where the leading edge 66 is concave (female) and the leading edge 76 is convex (male). Additional forms are contemplated where at least one or the leading edges or trailing edges of the first absorbent core layer 60 and/or the second absorbent core layer 70 are neither convex nor concave, e.g. substantially flat.

Referring back to FIG. 5, from the cutting device 530A, the plurality of discrete first absorbent cores 560A is provided to a cut-and-slip or cut-and-lay operation 540A. The cut-and-slip or cut-and-lay operations position each of the plurality of discrete first absorbent cores 560A onto a carrier web at spaced apart intervals. The carrier web will be described in additional detail hereafter. The first absorbent core 60 (shown in FIGS. 3 and 4) that is placed onto the carrier web, may be oriented such that the convex (male) end is the leading edge in the machine direction or the concave (female) end is the leading edge.

Similarly, from the cutting device 530B, the plurality of discrete second absorbent cores 570A is provided to a cut-and-slip or cut-and-lay operation 540B. The cut-and-slip or cut-and-lay operations 540B position each of the plurality of discrete second absorbent cores 570A onto the carrier web at spaced apart intervals. As shown, the second absorbent core 70 (shown in FIGS. 3 and 4) can be placed onto the carrier web post the addition of the first absorbent core 60 to the carrier web forming a laminate structure web. In such forms, the second absorbent core 70 may be provided in an offset manner such that its upper surface 70A (shown in FIG. 4) is attached to the lower surface 60B of the first absorbent core 60. The second absorbent core 70 and the first absorbent core 60 may be attached in any suitable manner, e.g. adhesives.

It is worth noting that where the first absorbent core 60 and the second absorbent core 70 are positioned in an offset manner and are adhesively attached, care should be taken as to how the adhesive is applied. Referring now to FIGS. 4 and 5, adhesive applied to the lower surface 60B should be strategically positioned to reduce the likelihood of contamination of the equipment. For example, as shown, adhesive applied in the front end portion 205F could contaminate the equipment as the second absorbent core layer 70 does not overly the adhesive in that area. Adhesive is needed in the central portion 205C. Additionally, adhesive should be provided in the rear end portion 205R. In such forms, adhesive would be applied to the carrier web to ensure that the second absorbent core 70 releases completely from the cut-and-slip or cut-and-lay operation 540B. In other forms where the second leading edge 76 forms the front end portion 205F, adhesive should be applied to the carrier web in this area to ensure that the second leading edge 76 is released from the cut-and-slip or cut-and-lay operation 540B. Cut-and-slip and cut-and-lay devices are well known in the art.

Still referring to FIGS. 4 and 5, from the second cut-and-slip or cut-and-lay operation 540B, a laminate structure web 581 comprising the carrier web, first absorbent core 60 and the second absorbent core 70 is provided. From here, a backsheet web can be provided over the lower surface 70B of the second absorbent layer 70. The backsheet web can cover the laminate structure web 581. The backsheet web and the carrier web can then be joined to encapsulate the first absorbent core layer 60 and the second absorbent core layer 70 thereby forming an absorbent article web. The absorbent article web can then be provided to a cutting device which cuts the absorbent article web into individual absorbent articles.

Figure 7:
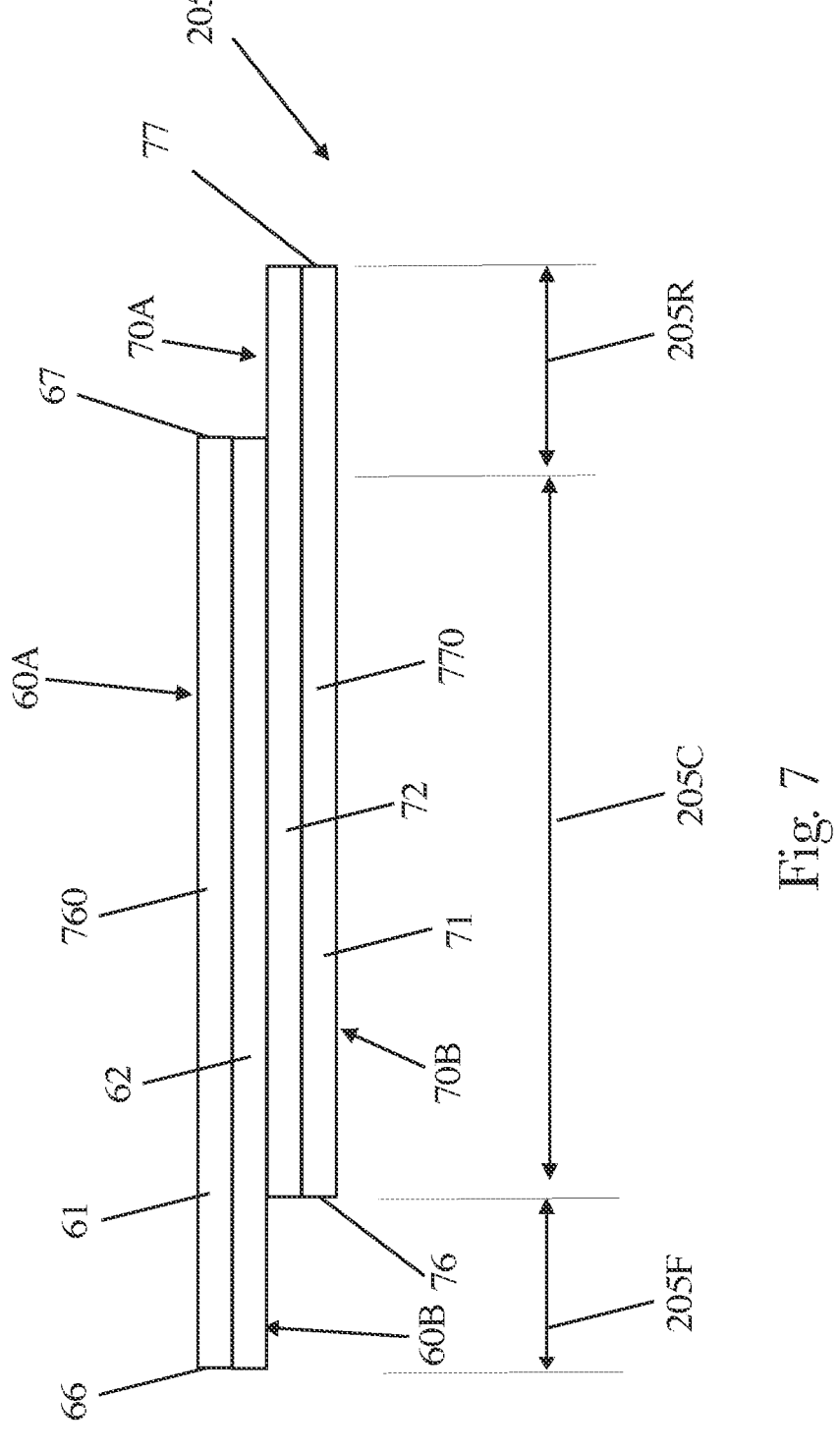
FIG. 7 is an elevation view showing another exemplary absorbent system in accordance with the present disclosure.

In some forms, as mentioned previously, the first absorbent core 60 and/or the second absorbent core 70 may comprise a plurality of webs and/or layers themselves, i.e. laminate structures. Referring now to FIG. 7, for example, the first absorbent core 60 (shown in FIGS. 3 and 4) may comprise a first superabsorbent layer 61 disposed on a first distribution layer 62, i.e. a first absorbent core laminate 760. And, the second absorbent core 70 (shown in FIGS. 3 and 4) may comprise a second superabsorbent layer 71 disposed on a second distribution layer 72, i.e. a second absorbent core laminate 770. In some forms, the first distribution layer 62 is joined to the second distribution layer 72 in an offset manner or configuration along the length of the core. This offset joinder of the first and second distribution layers 62, 72 results in an overlapping and joined area of the two laminates that forms a central portion 205C of the absorbent system 205. The central portion 205C of the absorbent system 205 is consequently bounded on each side by a front end portion 205F and a rear end portion 205R, both of the core. In other words, the front end portion 205F and the rear end 205R portion are respectively disposed at opposing ends of the absorbent system 205. As shown, the front end portion 205F is formed from the first leading edge 66 of the first absorbent core laminate 760 while the rear end portion 205R of the core 205 is formed by the second trailing edge 77 of the second absorbent core laminate 770.

For the form of FIG. 7, the first leading edge 66 and second trailing edge 77 of the first and second absorbent core laminates, respectively, oppose each other and form the front end portion 205F and the rear end portion 205R of the absorbent system 205, respectively or vice versa. In other forms, the first trailing edge 67 and second leading edge 76 of the first and second absorbent core laminates may oppose each other and form a front end portion 205F and a rear end portion 205R of the absorbent system 205, respectively or vice versa. In both instances, the first leading edge 66 and second trailing edge 77 may be in the form of a male connection derived from a nested cut of the first and second absorbent cores. Similarly, the first trailing edge 67 and second leading edge 76 may be in the form of a female connection derived from a nested cut of the first and second laminates, respectively. The nested cuts of the leading edges and trailing edges of the first and second absorbent core laminates are discussed in additional detail hereafter.

In an alternate form, the first absorbent core laminate 760 may be joined to superabsorbent layer 71 instead of the second distribution layer 72. In such forms, the laminates may be joined to one another in an offset manner as well except the first distribution layer 62 is joined to the second superabsorbent layer 71 instead of the second distribution layer 72.

In some forms, the overlapping area or region that forms the central portion 205C of the core 205 has at least one characteristic of a greater capacity, a greater void volume, or a greater thickness than the front end portion 205F and the rear end portion 205F of the absorbent system 205. These forms may be particularly useful for providing for heightened leakage protection in the central portion where female users of such pads would typically contact the pad and release fluids.

Referring back to FIG. 4, as noted previously, the first absorbent core 60 and/or the second absorbent core 70 may comprise laminate structures. However, in some forms, the first absorbent core 60 and second absorbent core layer 70 may comprise airlaid structures. However, the utilization of airlaid structures may obviate the need for separate distribution layers and superabsorbent layers. In other examples, at least one of the first absorbent core layer 60 or second absorbent core layer 70 may comprise a laminate structure as described above with regard to FIG. 7 while the other of the first absorbent core layer 60 or second absorbent core layer 70 comprise an airlaid structure. Suitable airlaid absorbent core structures are disclosed in U.S. Pat. Nos. 8,105,301 and 8,603,622 and U.S. Patent Application Publication No. 2017/0348166.

Figure 8:
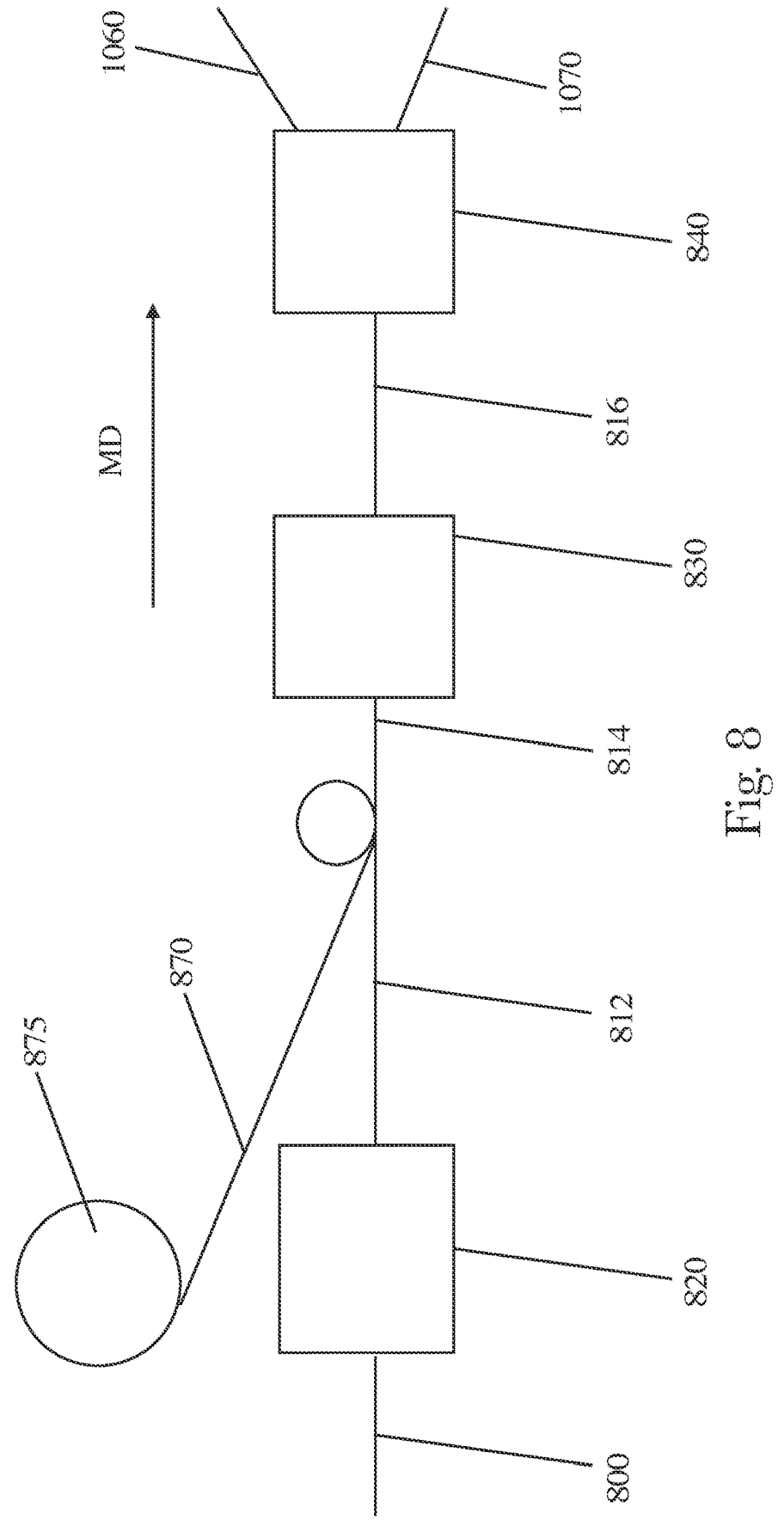
FIG. 8 is a process schematic showing another exemplary process in accordance with the present disclosure.

For those forms where the first absorbent core and/or the second absorbent core comprise a laminate structure, processing of such forms can be facilitated according to the process of the present disclosure. As shown in FIG. 8, a carrier web 800 can be obtained from a supplier or can be manufactured by an absorbent article manufacturer. Additional details of the carrier web 800 will be provided hereafter. As shown, the carrier web 800 can be transported in a machine direction to a composition deposition apparatus 820. In some forms, the composition deposition apparatus 820 can deposit superabsorbent material onto the carrier web 800. In some forms, the composition deposition apparatus 820 can deposit a mixture of materials, e.g. superabsorbent, cellulose, stiffening fibers, etc. In some forms, the composition apparatus can deposit health benefit agents onto the carrier web 800. In some forms, multiple composition deposition apparatuses may be utilized. Composition deposition apparatuses are known in the art examples of which are available from Christy Machine & Conveyor in Fremont, OH. Additional examples of composition deposition apparatuses are described in U.S. Pat. Nos. 7,838,722; 8,180,603; 7,744,713; 8,206,533; 8,568,566; and U.S. Patent Application Publication No. 2015/0223990A1.

Figure 9A:
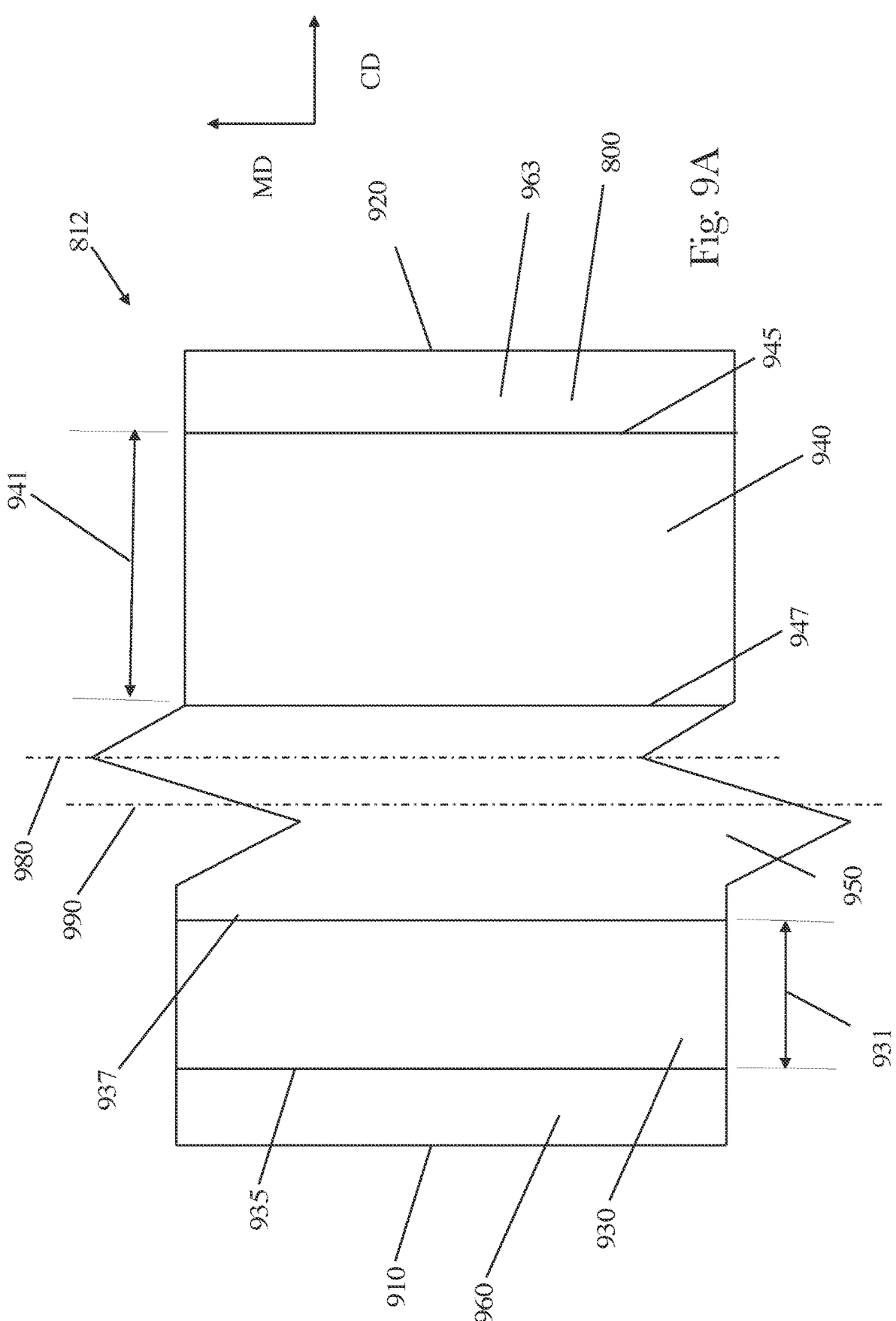
FIG. 9A is a plan view showing a carrier web with first and second compositions thereon in accordance with the present disclosure.
Figure 9B:
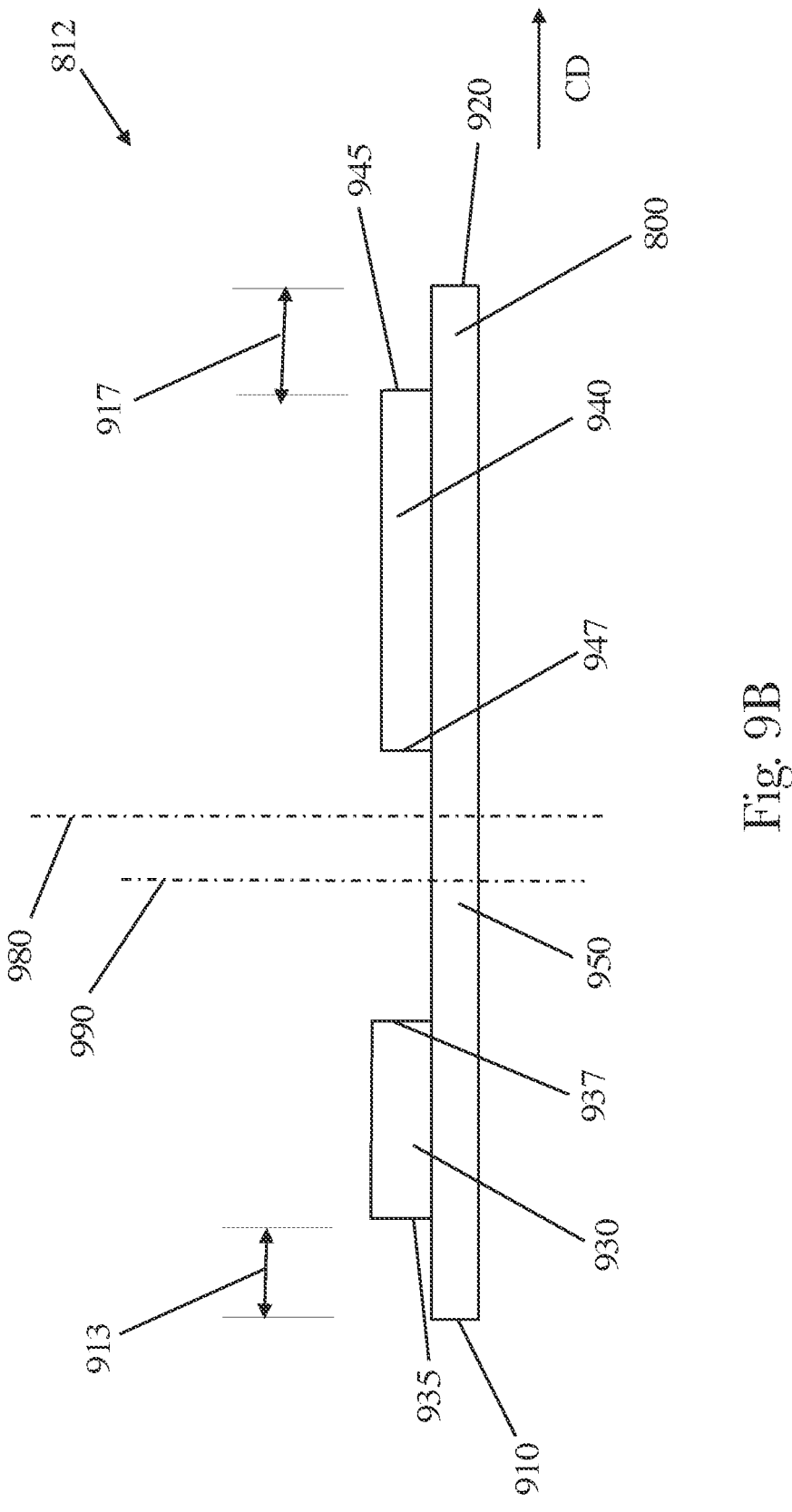
FIG. 9B is a cross sectional view of the carrier web with first and second compositions shown in FIG. 9A.
Figure 10:
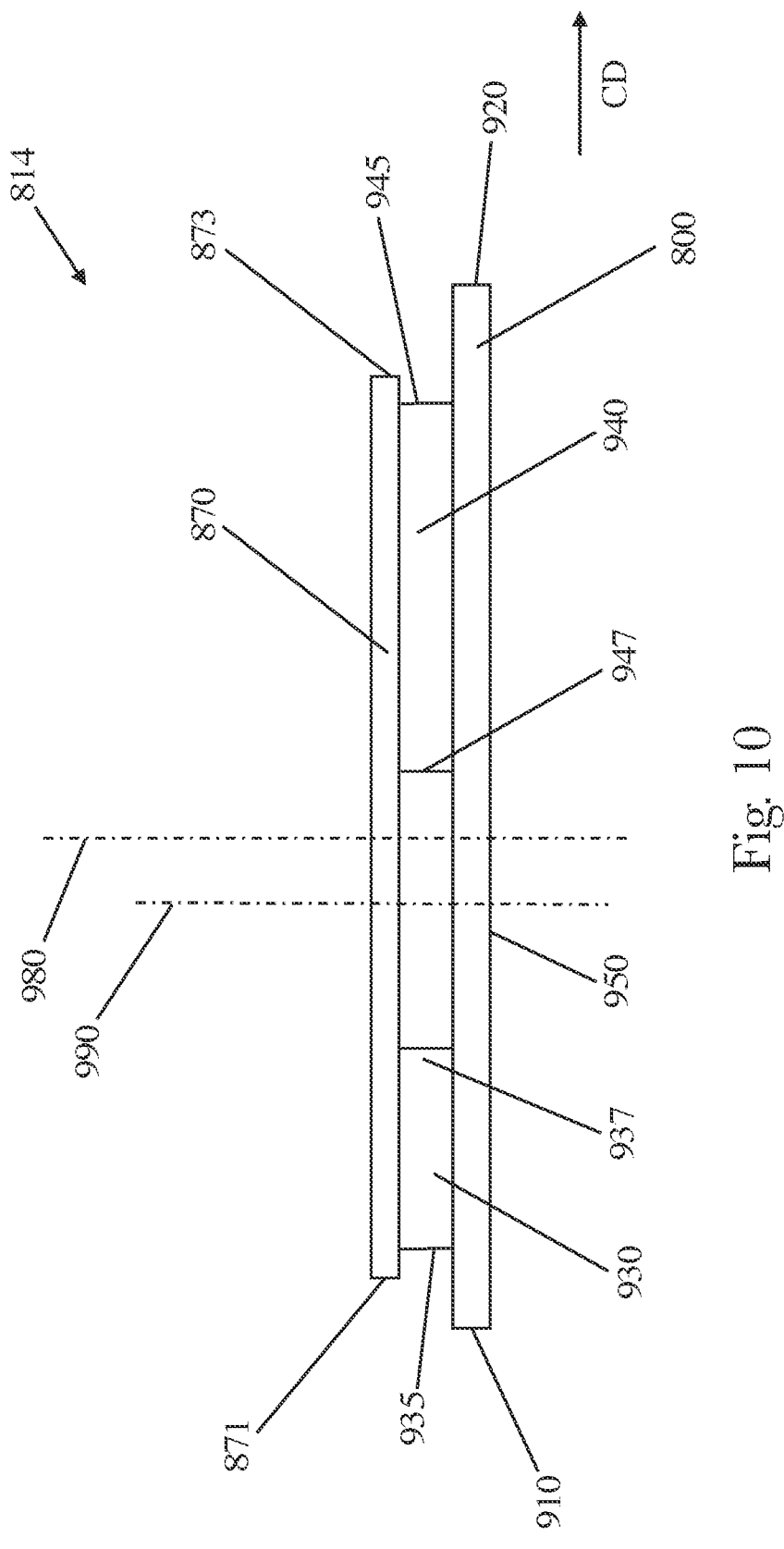
FIG. 10 is a cross sectional view of the carrier web of FIG. 9B with the additional feature of a support web in accordance with the present disclosure.
Figure 11:
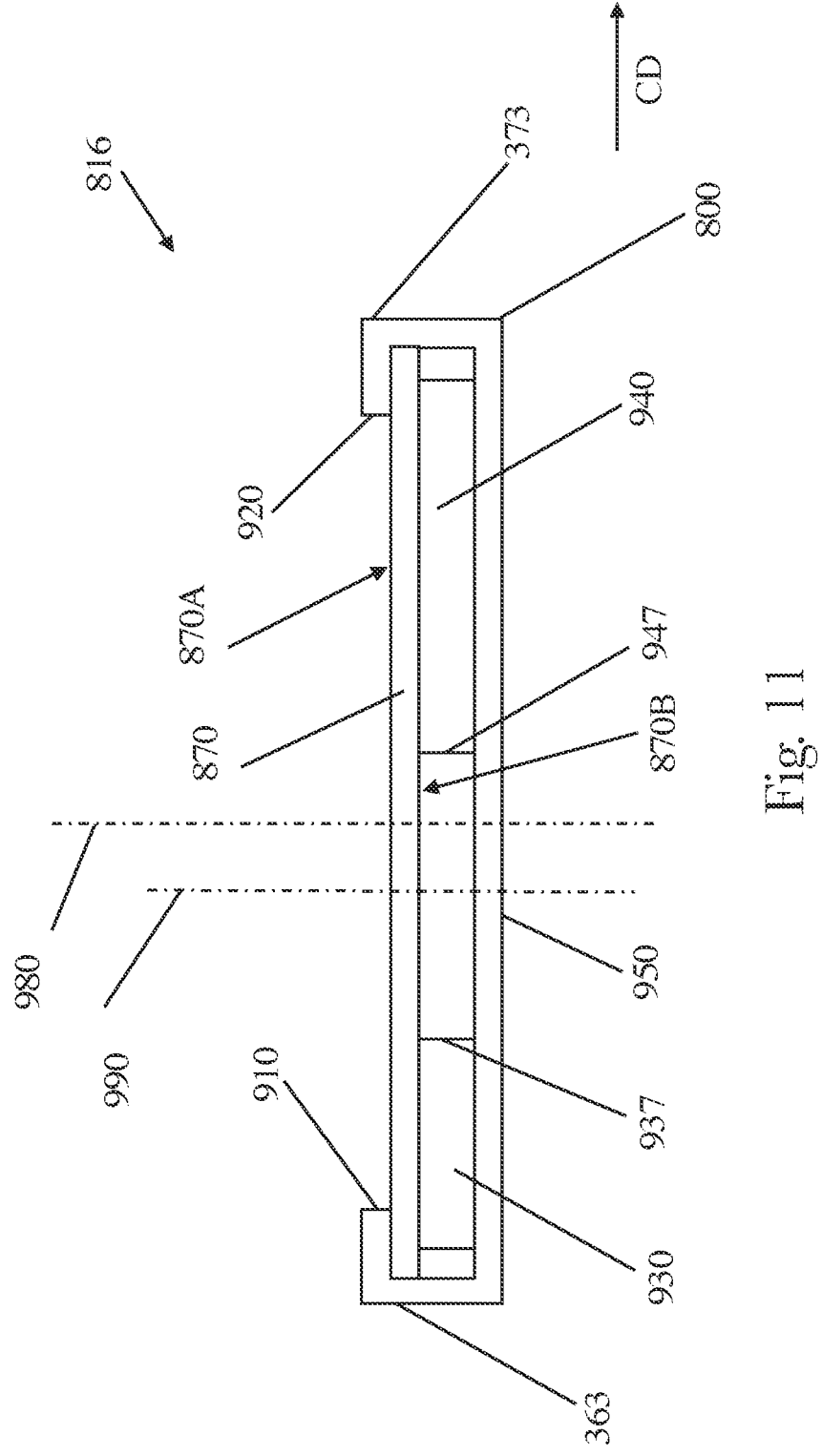
FIG. 11 is a cross sectional view of the web of FIG. 10 with the added features of the first and second outer edges.

Referring now to FIGS. 8 through 9B, the composition deposition apparatus 820 can deposit a first composition lane 930 and a second composition lane 940 on the carrier web 800 on a first portion 960 and second portion 963, respectively, thereby forming a composition web 812. As shown, the composition web 812 comprises a first edge 910 and an opposing second edge 920. The first and second edges 910 and 920 of the composition web 812 run generally parallel to the machine direction. The first composition lane 930 comprises a first proximal edge 935 which is adjacent the first edge 910 of the composition web 812 and a first distal edge 937 which is disposed opposite the first proximal edge 935 and is disposed adjacent a slit line 990. And, similar to the first edge 910 and second edge 920 of the composition web 812, the first proximal edge 935 and the first distal edge 937 are generally oriented parallel to the machine direction. A first composition width 931 is defined by an average distance between the first proximal edge 935 and the first distal edge 937.

As shown, the second composition lane 940 is spaced apart from the first composition lane 930 in the cross machine direction. An intermediate lane 950 is disposed between the first composition lane 930 and the second composition lane 940. Similar to the first composition lane 930, the second composition lane 940 comprises a second proximal edge 945 which is adjacent to the second edge 920 of the composition web 812. Opposite the second proximal edge 945, a second distal edge 947 is disposed adjacent to a centerline 980 of the composition web 812. The second proximal edge 945 and the second distal edge 947 are generally oriented parallel to the machine direction. A second composition width 941 is defined by an average distance between the second proximal edge 945 and the second distal edge 947. In some forms, a ratio of the first composition width 931 to the second composition width 941 can be from about 1 to 1, 0.9 to 1; 0.7 to 1; 0.5 to 1, specifically including all values within these ranges and any ranges created thereby.

The intermediate lane 950 has a width which is defined by the average distance between the first distal edge 937 and the second distal edge 947. In some forms, the intermediate lane 950 width can be less than about 11 mm, less than about 9 mm, less than about 7 mm, less than about 6 mm, less than about 4 mm, specifically reciting all values within these ranges and any ranges created thereby. However, it is believed that a minimum width should be about 3 mm. The 3 mm width of the intermediate lane 950 may allow for appropriate processing of the composition web 812. For example, where the composition deposited is a particulate material, the first edge 910 and second edge 920 of the composition web 812 may need to be folded or otherwise sealed to encapsulate the particulate material. Such folding or sealing can reduce the likelihood of contamination of the processing equipment by the particulate material. The inventors believe that below a 3 mm width (1.5 mm allowance for the first composition lane and 1.5 allowance for the second composition lane) that such contamination reduction measures may be much more difficult to achieve.

Referring now to FIGS. 8 through 11, subsequent the formation of the composition web 812, a support web 870 is provided to the composition web 812. The support web 870 may be produced by a consumer goods manufacturer or may obtained from a supplier of such materials. As shown, the support web 870 may be provided by a roll 875 of support web material. The support web 870 is provided on an upper surface of the first composition lane 930 and on an upper surface of the second composition lane 940 thereby forming an absorbent core web 814. The support web 870 comprises a first surface 870A and an opposing second surface 870B.

The support web 870 can have a first support web edge 871 and a second support web edge 873 opposite the first support web edge 871. The first support web edge 871 and the second support web edge 873 extend generally parallel to the machine direction. As shown, the support web 870 may overlap the first composition lane 930 and the second composition lane 940 such that the first support web edge 871 is disposed outboard of the first proximal edge 935 and the second support web edge 873 is disposed outboard of the second proximal edge 945.

In some forms, after the application of the support web 870 to the composition web 812, the absorbent core web 814 is folded via a folding unit operation 830 such that the first edge 910 of the carrier web 800 is folded over and attached to the first surface 870A of the support web 870. Folding the first edge 910 forms the first outer edge 363. Similarly, the second edge 920 of the carrier web 800 may be folded over and attached to the first surface 870A of the support web 870. Folding the second edge 920 forms the second outer edge 373. The absorbent core web 814 post the folding unit operation 830 is the folded absorbent core web 816.

Folding unit operations are well known in the art of absorbent article manufacture. However, for those forms where the carrier web 800 is sealed to the support web 870 to form outer edges 363 and 373, a distance between the first edge 910 of the carrier web 800 and the first proximal edge 835 may need to be carefully planned. Again, where the composition that is imparted onto the carrier web 800 is particulate material, the creation of outer edges 363 and 373, whether via folding of the carrier web 800, folding of the support web 870, or sealing the edges of the carrier web 800 and support web 870 together, can reduce the likelihood of contamination of the equipment. In some forms, a first offset distance 913 between the first edge 910 and the first proximal edge 935 can be at least about 3 mm, greater than 3 mm, greater than 7 mm, greater than 10 mm, greater than 13 mm, or at least 17 mm, specifically including all values within these ranges and any ranges created thereby. A second offset distance 917 between the second edge 920 and the second proximal edge 945 may be similarly configured as the first offset distance 913. It is worth noting that a larger offset distance, e.g. 913 and/or 917, can impact the amount of composition in the first lane 930 and/or the amount of composition in the second lane 940. Accordingly, the offset distances 913 and 917 should be less than about 35 mm, less than about 30 mm, or less than about 25 mm, specifically reciting all values within these ranges and any ranges created thereby.

Additionally, in conjunction with the first offset distance 913 and/or second offset distance 917, or independent thereof, a distance between the first proximal edge 935 and the first support web edge 871 can be at least about 2.5 mm, at least about 3 mm, or at least about 4.5 mm, specifically including all values within these ranges and any ranges created thereby. A distance between the second proximal edge 945 and the second support web edge 873 may be configured similarly. Again, the above values can facilitate the creation of the outer edges 363 and 373 which can reduce the likelihood that particulate material in the first and/or second composition lanes contaminate processing equipment. However, much like the larger offset distances mentioned previously, larger distances between the proximal edges and the support web edges can have an impact on the amount of composition in the first lane 930 and/or second lane 940. Accordingly, these distances should be less than about 35 mm, less than about 25 mm, or less than about 15 mm, specifically reciting all values within these ranges and any ranges created thereby.

After the creation of the outer edges 363 and 373, the folded absorbent core web 816 may then be provided to a slitting unit operation 840. Slitting unit operations are well known in the art. Still referring to FIGS. 8-11, the slitting operation can cut the folded absorbent core web 816 along a slit line 990 which in some forms, may be offset from a centerline 980 of the folded core web 816. In some forms, the slit line 990 may be colinear with the longitudinal centerline 980. As shown, post slitting, two separate webs may be created, namely, a first absorbent core web 1060 and a second absorbent core web 1070. Additionally, in some forms, edges of the carrier web 800 and support web 870 created via the slitting operation may be sealed together, e.g. folded, similar to the outer edges 363 and 373 to reduce the likelihood of contamination by compositions in the first lane 930 and/or second lane 940.

Figure 12:
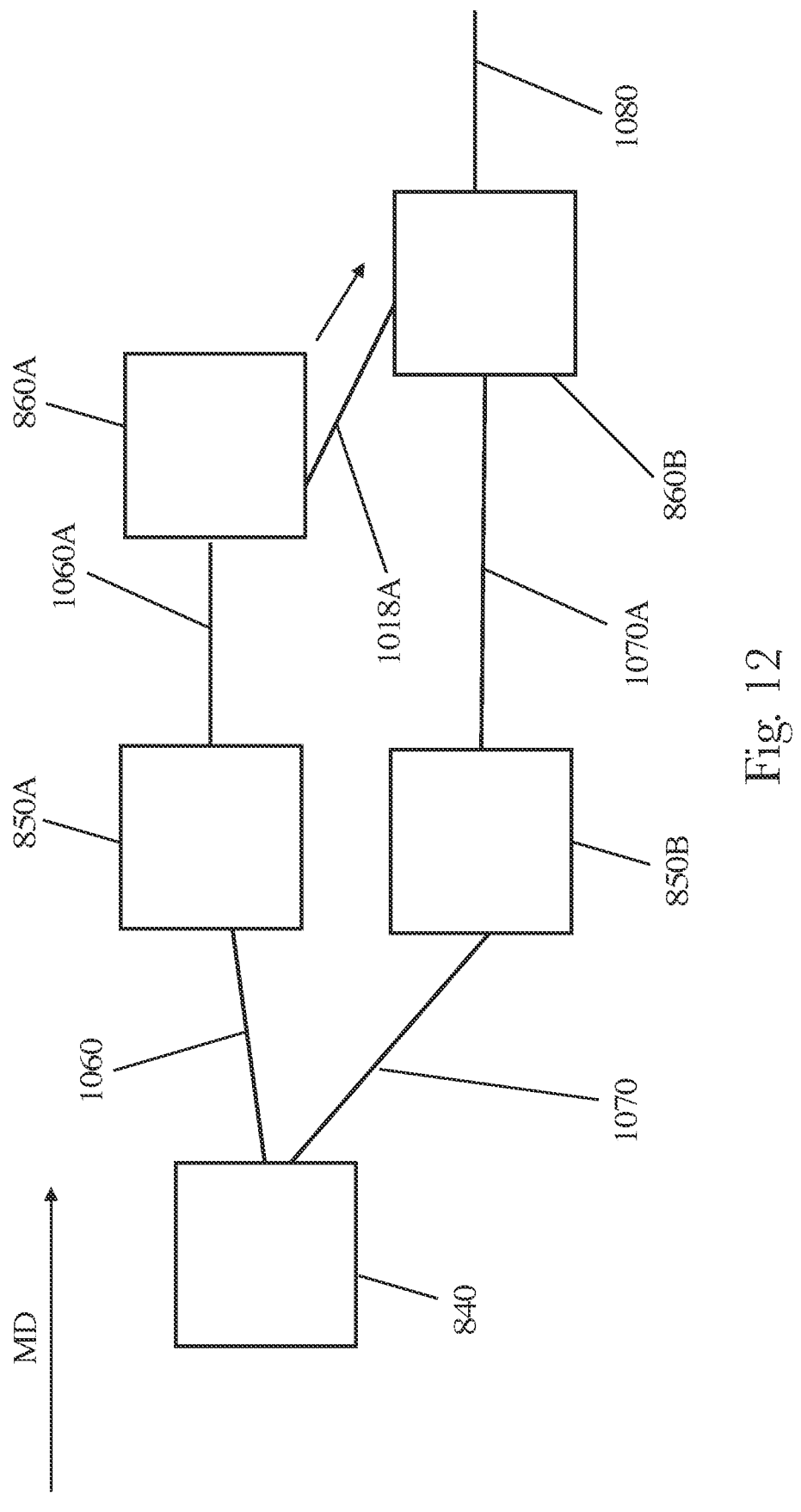
FIG. 12 is a process schematic showing additional processes to the process of FIG. 8, in accordance with the present disclosure.

Referring now to FIG. 12, the first absorbent core web 1060 may then be provided to a cutting device 850A while the second absorbent core web 1070 may be provided to a second cutting device 850B. The first cutting device 850A creates a plurality of discrete first absorbent cores 1060A from the first absorbent core web 1060. The second cutting device 850B creates a plurality of discrete absorbent cores 1070A from the second absorbent core web 1070. Exemplary cutting devices are disclosed in U.S. Patent Application Publication No. 2018/0154533.

For the sake of clarity, individual first absorbent cores 1060A of the plurality may be referred to as the first absorbent core laminates 760 (shown in FIG. 7), and individual second absorbent cores 1070A of the plurality may be referred to as the second absorbent cores 770 (shown in FIG. 7). As each of the plurality of first absorbent cores 1060A and second absorbent cores 1070A may be constructed as described herein with regard to the first absorbent cores 760 and the second absorbent cores 770, such designation facilitates discussion.

It is worth noting that while the slit edge can be created as disclosed herein, it is not necessarily required. Absorbent article manufacturers can obtain the first absorbent core web 1060 and/or a second absorbent core web 1070 via processing described herein or could receive the first absorbent core web and/or the second absorbent core web separate. In such instances, the need to slit the absorbent core web would be obviated.

Referring now to FIGS. 3, 7, and 12 as shown, the cutting device 850A can provide the first absorbent core 760 with a convex (male) leading edge 66 while the second cutting device 850B can provide the second absorbent core 770 with a concave (female) leading edge 76. However, forms are contemplated where both the leading edges 66 and 76 are convex (male). Forms are contemplated where both the leading edges are concave (female). Forms are contemplated where the leading edge 66 is concave (female) and the leading edge 76 is convex (male). Additional forms are contemplated where at least one or the leading edges or trailing edges of the first absorbent core 760 and/or the second absorbent core 770 are neither convex nor concave, e.g. substantially flat.

It is worth noting that where convex and concave edges are desired on the ends of the absorbent cores, whether single layers or laminates, care should be taken with regard to the cross machine direction tracking. If the web enters into the cutting device such that the web centerline does not match the cutting device centerline in the machine direction, then the curvature on the concave edges could be skewed. This skewed edge could create one side of the edge having a tail, e.g. a longer end. If too long of a tail is created, then part of the core could end up in a perimeter product seal (crimp) which could lead to a quality defect. To minimize the likelihood of this quality defect, the centerline of the webs entering the cutting device should be within 1 sigma value, i.e. plus or minus 2.5 mm of the cutting device centerline. Where entering web are outside of this 1 sigma value, a web tracking device can be utilized to correct the tracking of the entering web such that the desired tolerances are achieved. Web tracking devices are known in the art.

Referring back to FIG. 12, from the cutting device 850A, the plurality of discrete first absorbent cores 1060A is provided to a cut-and-slip or cut-and-lay operation 860A. The cut-and-slip or cut-and-lay operation can position each of the plurality of discrete first absorbent cores 1060A (individually referred to as first absorbent cores 760) on a wearer-facing web, e.g. a topsheet web, a secondary topsheet web, or on a combination web of the topsheet and secondary topsheet at spaced apart intervals. The placement of the discrete first absorbent cores 1060A onto the wearer-facing web forms a hybrid web 1018A. In some forms, the carrier web 800 (shown in FIGS. 9A-11 and 13) may be the wearer-facing web. Additional details regarding the carrier web are provided hereafter. The first absorbent core 760 (shown in FIG. 7) that is placed onto the web, may be oriented such that the convex (male) end is the leading edge in the machine direction or the concave (female) end is the leading edge.

Similarly, from the cutting device 850B, the plurality of discrete second absorbent cores 1070A is provided to a cut-and-slip or cut-and-lay operation 860B. The cut-and-slip or cut-and-lay operation 860B can position each of the plurality of discrete second absorbent cores 1070A (individually referred to as second absorbent cores 770) onto the hybrid web 1018A at spaced apart intervals. In such forms, the second absorbent core 770 may be provided in an offset manner such that its upper surface 70A (shown in FIG. 7) is attached to the lower surface 60B of the first absorbent core 760. The second absorbent core 770 and the first absorbent core 760 may be attached in any suitable manner, e.g. adhesives.

It is worth noting that where the first absorbent core 760 and the second absorbent core 770 are positioned in an offset manner and are adhesively attached, care should be taken as to how the adhesive is applied. Referring back to FIG. 7, adhesive applied to the lower surface 60B should be strategically positioned to reduce the likelihood of contamination of the equipment. For example, as shown, adhesive applied in the front end portion 205F could contaminate the equipment as the second absorbent core 770 does not overly the adhesive in that area. Adhesive is needed in the central portion 205C. Additionally, adhesive should be provided in the rear end portion 205R. In such forms, adhesive would be applied to the carrier web to ensure that the second absorbent core 770 releases completely from the cut-and-slip or cut-and-lay operation 860B. In other forms where the second leading edge 76 forms the front end portion 205F, adhesive should be applied to the carrier web in this area to ensure that the second leading edge 76 is released from the cut-and-slip or cut-and-lay operation 860B. Cut-and-slip and cut-and-lay devices are well known in the art.

Figure 13:
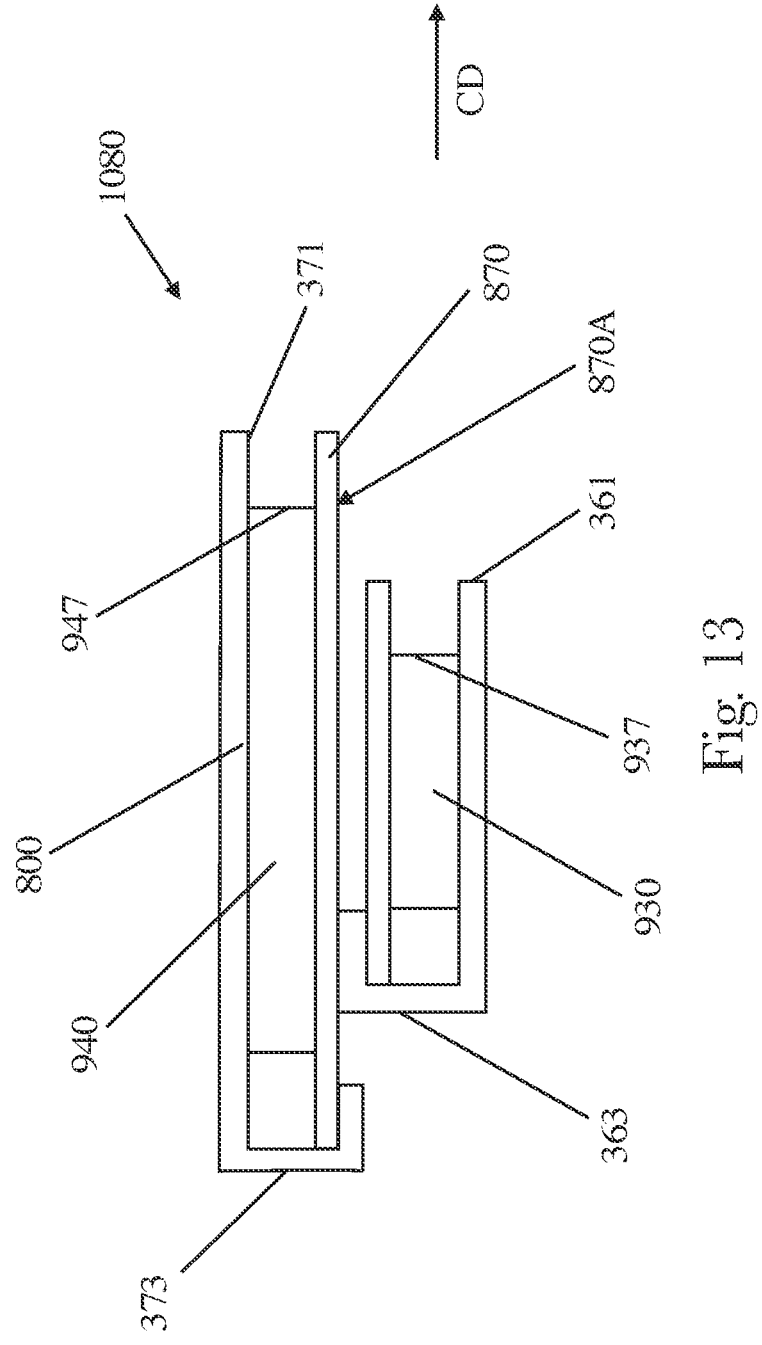
FIG. 13 is a cross sectional view showing the web of FIG. 11 after being split into a first and second absorbent core laminates.

In some forms, the cut-and-slip or cut-and-lay operation 860B can invert the second absorbent core 770. For example, as shown in FIGS. 7, 12, and 13, the second absorbent core 770 can be rotated about an axis that is generally parallel to the machine direction. The combination of the first absorbent core 760 and the second absorbent core 770 creates a laminate structure web 1080. In some forms of the laminate structure web 1080, the first and second outer edges 363 and 373 are positioned on the same side. And opposite the first and second outer edges 363 and 373, the first slit edge 361 and the second slit edge 371 are positioned on the same side of the laminate structure web 1080. Still in other forms, the second absorbent core 770 may be placed on the first absorbent core 760 such that the carrier web of the second absorbent laminate is in contact with the support web 870 of the first absorbent core 760, e.g. the first and second outer edges 363 and 373 are disposed on opposite sides of the laminate structure web 1080. In such executions, once incorporated into an absorbent article, the first and second outer edges 363 and 373 would be positioned on opposite sides of a longitudinal axis of the absorbent article.

From the second cut-and-slip or cut-and-lay operation 860B, the laminate structure web 1080 comprising the first absorbent core 760 and the second absorbent core 770 is provided. And as noted previously, in some forms, the laminate structure web 1080 may comprise the wearer-facing web in combination with the foregoing. From here, a backsheet web can be provided over the lower surface 70B of the second absorbent core 770. The backsheet web can cover the laminate structure web 1080. The backsheet web and the carrier web and/or wearer-facing web can then be joined to encapsulate the first absorbent core 760 and the second absorbent core 770 thereby forming an absorbent article web. The absorbent article web can then be provided to a cutting device which cuts the absorbent article web into individual absorbent articles.

The inventors have also found that either upstream or downstream of the cut and slip and/or cut and lay operations described herein in FIGS. 5 and 12, that core orientation may be monitored to reduce the likelihood of mis-oriented cores. For example, where the first superabsorbent layer and/or the second super absorbent layer are desired to be oriented more proximal to the wearer, a vision sensor may be utilized. Or, even where the first distribution layer and/or the second distribution layer are desired to be more proximal to the wearer, a vision sensor may be utilized. While a vision system may be utilized to determine the orientation of the absorbent layers of the absorbent articles of the present disclosure, vision systems can be bulky and costly to purchase and operate. In contrast, a vision sensor can cost considerably less than a vision system and may not require the space of the vision system.

The vision sensor can be programmed to recognize the texture of opposing sides of the superabsorbent layers. For example, the carrier web utilized herein can be fairly smooth. In contrast, the compositions deposited upon the carrier web, e.g. AGM, can have a much rougher surface. The vision sensor can be programmed to "see" the difference in the roughness of the carrier web versus that of the composition deposited thereon. In doing so, the vision sensor can then provide a binary output, e.g. a 1 or 0, to a central processing unit (CPU). The signal can be a 0 for the correct orientation versus a 1 for the incorrect orientation. Additionally, the CPU can be programmed such that the CPU monitors a moving average of articles, e.g. articles 1-101, then 2-102, etc. The moving average can be utilized to determine if the incorrect orientation, e.g. a 1, is sustained for more than simply a few articles. Any suitable vision sensor may be utilized. One specific example includes the vision sensor available from Keyence and sold under the trade name IV-HG500MA.

Applicant shall now provide more detailed insight into the individual components of the disposable absorbent articles envisioned herein.

Primary Topsheet

Referring back to FIG. 2, the primary topsheet 203 (also referred to herein "topsheet") of the chassis 20 is positioned adjacent a body-facing surface 203A of the absorbent system 205 and may be joined thereto and to the backsheet 207 by attachment methods (not shown) such as those well known in the art. Suitable attachment methods are described with respect to joining the backsheet 207 to the absorbent system 205. The topsheet 203 and the backsheet 207 may be joined directly to each other in the incontinence pad periphery and may be indirectly joined together by directly joining them to the absorbent system 205 or additional optional layers within the chassis like a secondary topsheet which spans the entire or partial area of the article. This indirect or direct joining may be accomplished by attachment methods which are well known in the art.

The absorbent article may comprise any known or otherwise effective primary topsheet, such as one which is compliant, soft feeling, and non-irritating to the wearer's skin. Suitable primary topsheet materials include a liquid pervious material that is oriented towards and contacts the body of the wearer permitting bodily discharges to rapidly penetrate through it without allowing fluid to flow back through the topsheet to the skin of the wearer. The primary topsheet, while being capable of allowing rapid transfer of fluid through it, also provides for the transfer or migration of the lotion composition onto an external or internal portion of a wearer's skin. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof. Some suitable examples of films that can be utilized as topsheets are described in U.S. Pat. Nos. 3,929,135; 4,324,246; 4,342, 314; 4,463,045; 5,006,394; 4,609,518; and 4,629,643.

Nonlimiting examples of woven and nonwoven materials suitable for use as the topsheet include fibrous materials made from natural fibers, modified natural fibers, synthetic fibers, or combinations thereof. Some suitable examples are described in U.S. Pat. Nos. 4,950,264, 4,988,344; 4,988,345; 3,978,185; 7,785,690; 7,838,099; 5,792,404; and 5,665,452.

In some forms, the topsheet may comprise tufts as described in U.S. Pat. Nos. 8,728,049; 7,553,532; 7,172, 801; 8,440,286; 7,648,752; and 7,410,683. The primary topsheet may have a pattern of discrete hair-like fibrils as described in U.S. Pat. No. 7,655,176 or 7,402,723. Additional examples of suitable topsheet includes those described in U.S. Pat. Nos. 8,614,365; 8,704,036; 6,025,535 and in U.S. Patent Application Publication No. 2016/0129661.

Another suitable primary topsheet or a primary topsheet combined with a secondary topsheet may be formed from a three-dimensional substrate as detailed in a U.S. Patent Application Publication No. 2017/0258647 A1.

The primary topsheet may have one or more layers, as described in U.S. Patent Application Publication Nos. 2016/ 0167334 A1; 2016/0166443 A1; 2017/0258651 A1. The topsheet may be apertured as disclosed in U.S. Pat. No. 5,628,097, to Benson et al., issued on May 13, 1997.

Secondary Topsheet

As noted previously, the disposable absorbent articles of the present disclosure may comprise additional layers, one of which includes a secondary topsheet. As mentioned previously, the secondary topsheet may be separate and apart from the absorbent system. Additionally, the secondary topsheet is disposed beneath the primary topsheet 203 and on the body-facing surface of the core. In some forms, the secondary topsheet may have a basis weight from about 40 gsm to about 100 gsm, from about 45 gsm to about 75 gsm, or from about 50 gsm to about 60 gsm, specifically including all values within these ranges and any ranges created thereby. In some forms, the secondary topsheet may comprise a homogeneous mix of fibers.

Some exemplary secondary topsheets are described in U.S. Patent Application Publication Nos. 2015/0351976 A1 and 2014/0343523 A1; and U.S. Patent Application Serial No. 2018/0098893. Forms are contemplated where the carrier web 800 (shown in FIGS. 9B-11) comprises a secondary topsheet.

Backsheet

The backsheet 207 of the chassis 20 may be positioned adjacent a garment-facing surface of the absorbent system 205 and may be joined thereto by attachment methods (not shown) such as those well known in the art. For example, the backsheet 207 may be secured to the absorbent system 205 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent system 205 is not joined to the backsheet 207, the topsheet 203, or both.

The backsheet 207 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent system 205 from wetting articles of clothing which contact the incontinence pad 10 such as undergarments. However, in some instances, the backsheet 207 may permit vapors to escape from the absorbent system 205 (i.e., is breathable) while in other instances the backsheet 207 may not permit vapors to escape (i.e., non-breathable). Thus, the backsheet 207 may comprise a polymeric film such as thermoplastic films of polyethylene or polypropylene. A suitable material for the backsheet 207 is a thermoplastic film having a thickness of from about 0.012 mm (0.5 mil) to about 0.051 mm (2.0 mils), for example. Any suitable backsheet known in the art may be utilized with the present invention.

Some suitable examples of backsheets are described in U.S. Pat. Nos. 5,885,265; 4,342,314; and 4,463,045. Suitable single layer breathable backsheets for use herein include those described for example in GB A 2184 389, GB A 2184 390, GB A 2184 391, U.S. Pat. Nos. 4,591,523, 3,989,867, 3,156,242; WO 97/24097 and U.S. Pat. Nos. 6,623,464; 6,664,439 and 6,436,508.

The backsheet may have two layers: a first layer comprising a gas permeable aperture formed film layer and a second layer comprising a breathable microporous film layer as described in U.S. Pat. No. 6,462,251. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Absorbent System

The absorbent system 205 of the present invention may comprise any suitable shape including but not limited to an oval, a discorectangle, a rectangle, an asymmetric shape, and an hourglass. For example, in some forms of the present invention, the absorbent system 205 may comprise a contoured shape, e.g. narrower in the intermediate region than in the end regions. As yet another example, the absorbent system may comprise a tapered shape having a wider portion in one end region of the pad which tapers to a narrower end region in the other end region of the pad. The absorbent system 205 may comprise varying stiffness in the MD and CD.

As detailed earlier, the absorbent system 205 comprises the first absorbent core and the second absorbent core. And as described herein the first absorbent core and/or the second absorbent core may comprise a single layer or multiple layers. Both are generally compressible, conformable, non-irritating to the wearer's skin, and capable of absorbing and retaining liquids such as urine and other certain body exudates including menses.

The configuration and construction of the absorbent system 205 may vary (e.g., the absorbent system 205 may have varying caliper zones, a hydrophilic gradient, a superabsorbent gradient, or lower average density and lower average basis weight acquisition zones). Further, the size and absorbent capacity of the absorbent system 205 may also be varied to accommodate a variety of wearers. However, the total absorbent capacity of the absorbent system 205 should be compatible with the design loading and the intended use of the disposable absorbent article or incontinence pad 10.

In some forms of the present disclosure, the absorbent system 205 may comprise a plurality of multi-functional layers that are in addition to the first and second absorbent cores. For example, the absorbent system 205 may comprise a core wrap (not shown) useful for enveloping the first and second laminates and other optional layers. The core wrap may be formed by two nonwoven materials, substrates, laminates, films, or other materials. In a form, the core wrap may only comprise a single material, substrate, laminate, or other material wrapped at least partially around itself.

The absorbent system 205 of the present disclosure may comprise one or more adhesives, for example, to help immobilize the SAP or other absorbent materials within the first and second laminates.

Absorbent cores comprising relatively high amounts of SAP with various core designs are disclosed in U.S. Pat. No. 5,599,335 to Goldman et al., EP 1,447,066; WO 95/11652; U.S. Pat. Publ. No. 2008/0312622A1; and WO 2012/052172. These may be used to configure the superabsorbent layers.

Additions to the core of the present disclosure are envisioned. In particular, potential additions to the current multi-laminate absorbent core are described in U.S. Pat. Nos. 4,610,678; 4,673,402; 4,888,231; 4,834,735; 5,234,423; and 5,147,345. These are useful to the extent they do not negate or conflict with the effects of the below described layers of the absorbent core of the present invention.

The first and second absorbent cores layers and/or laminates of the absorbent system 205 have been detailed earlier but it is important to note that these layers or laminates may have cross-direction widths that are the same as each other or different. As discussed previously, for example, the first absorbent core layer or laminate may have a lesser cross-direction width than said second absorbent core layer or laminate or a greater cross-direction width than said second absorbent core layer or laminate. Forms are contemplated where the first and second absorbent core layers comprise the same width along at least a portion of their respective lengths. Some particular forms, the width of the absorbent core layers should have a width which is at least 2 mm narrower than the narrowest portion of the pad. This can help reduce the likelihood that either of the first absorbent core layer and/or second absorbent core layer end up in an area which is meant to be crimped/sealed. In general, if either of the absorbent core layers ends up in the crimp, then leaks could develop in those areas where the core is in the crimp. As leakage is generally perceived as a negative attribute by wearers of absorbent articles, leakage which is avoidable should be avoided.

In certain instances, the first and second absorbent core layers or laminates can have machine-direction lengths that are the same while in other instances, the first and second absorbent cores have machine-direction lengths that are different. In the latter instance, the first absorbent core layer or laminate may have a lesser machine-direction length than the second absorbent core layer or laminate, or conversely the first absorbent core layer or laminate may have a greater machine-direction length than said second absorbent core layer or laminate.

The first and second absorbent core layers or laminates in some forms, may further comprise an optional intermediate layer disposed between the respective superabsorbent layer and distribution layer. This optional intermediate layer may comprise materials detailed herein relative to the optional layers for the chassis, in general.

Additionally, in some forms, in addition to the first and second absorbent cores layers or laminates, the absorbent article or incontinence pad may further comprise an optional additional absorbent core comprising a superabsorbent layer and/or a distribution layer. This optional additional core may take the form of a third, fourth, fifth, or even additional layers. The superabsorbent layer and distribution layer may exhibit the same or different properties detailed earlier with respect to the first and second superabsorbent and distribution layers. Any optional additional cores may be disposed on a body-facing surface of the first absorbent core or second absorbent core or on a garment-facing surface of the first absorbent core or second absorbent core.

As stated previously, in some forms, the first absorbent core layer or laminate has a first leading edge 66 that is complementary in shape to its respective first trailing edge 67. More specifically, the first leading edge 66 of the first absorbent core layer or laminate may conform shapewise to the first trailing edge 67 of the same. The same conformance may apply to the second absorbent core layer or laminate. This conformation results from a nested cut of the first absorbent core layer or laminate and the second absorbent core layer or laminate that provides matching or shape fitting ends. Likewise, this feature may also be prevalent in any optional absorbent cores that might be incorporated into the absorbent system. This nesting or nested cut feature of the absorbent cores allow for reduced waste of trim during manufacture. It has also been found that it is possible to configure the first and second absorbent core layers or laminates in a manner that allows for their respective convex edges to oppose one another when the first and second distribution layers are overlapped and joined forming an absorbent system with a central portion 205C comprising an overlapping area.

Referring to FIGS. 3 and 7, as noted previously, the front end portion of the absorbent system 205F can be formed from a first leading edge 66 or second trailing edge 77 of either the first absorbent core or the second absorbent core. A rear end portion of the absorbent system 205R is similarly formed from a first leading edge 66 or the second trailing edge 77 of the other of the first absorbent core or the second absorbent core. This configuration yields an absorbent system with matching (i.e., a male connection) ends. In other forms, a front end portion of the absorbent system may be formed from a first leading edge 66 or a second trailing edge 77 of either the first absorbent core or the second absorbent core while the rear end portion of the absorbent system is formed from a first trailing edge 67 or a second leading edge 76 of the other of the first absorbent core or second absorbent core. In such forms, the second end is shaped as a female connection and therefore does not match the front end portion of the same core. In other forms, the front end portion of the absorbent system may be formed from the first trailing edge 67 of the first absorbent core or the second leading edge 76 of the second absorbent core. A rear end portion of the absorbent system may be similarly formed from the first trailing edge 67 of the remaining first absorbent core or the second leading edge 76 of the second absorbent core. This configuration yields an absorbent system with matching (i.e., a female connection) ends. It should be noted, however, that the width of the first and second absorbent cores may be the same or different as mentioned herein. The nested cuts of the leading edges and trailing edges of each of the first and second absorbent cores can have shapes selected from the group consisting of arcs, semicircles, semi-ellipses, chevrons, rectangles, sinusoids, jigsaws, and combinations thereof.

In some forms, the first or second absorbent cores may include one or more recessed areas that run along the machine direction or cross direction. These recessed areas may coincide with the discontinuous patterns of one or more of a superabsorbent layer and distribution layer, whether it be of the first absorbent core, second absorbent core, or both. These recessed areas may also merely be formed by embossing of the first or second absorbent cores. These recessed areas may alternatively be formed by slitting, cutting, ring-rolling, or otherwise providing mechanical deformation through the first and/or second absorbent cores. Each manner of recessed area formation mentioned herein is intended to yield a recessed area that is capable of providing a point of preferential bending of the overall article. For instance, a plurality of recessed areas either gaps or embossed channels may be provided in at least one or both of the first and second absorbent cores of absorbent system 205, in the machine direction. These recessed areas need not be present in both first and second absorbent cores along the entirety of each of their lengths. The recessed areas may be present in the machine direction only in the overlapping joinder area of the first and second absorbent cores. Alternatively, the recessed areas may be present in the in the cross direction along the length of the first and second absorbent cores, or only in the overlapping joinder of the two absorbent cores. In instances like these, the laminates through which the recessed areas are effected will be prone to bending more easily. In instances where a recessed area is present in only one of a first and second absorbent cores, it is expected that there will be a preferential tendency for the pad to bend at the recessed area. This means if the first absorbent core is closer to the body than the second absorbent core, the pad will likely bend away from the body. The opposite may be true as well in the event the second absorbent core placed away from the body comprises a recessed area and the first absorbent core does not. In this instance, the pad may exhibit preferential tendency to bend toward the body. Depending on the overall configuration of the pad, either type of bending may be preferred in a particular instance.

Additionally, for those forms where the first absorbent core and/or the second absorbent core do not comprise laminate structures, an airlaid core material can be utilized. Any suitable airlaid core can be utilized. Airlaid core material can be obtained by a manufacturer of such materials or can be made online via equipment known in the art. Where an airlaid core is utilized, the need for separate superabsorbent layers and distribution layers may be reduced.

Superabsorbent Layers

The first and second superabsorbent layers 61, 71 of the first and second absorbent cores 60, 70 comprise superabsorbent polymers or absorbent gelling materials (AGM). In some forms, the superabsorbent layer 61 and/or 71 may comprise the carrier web and composition. In such forms, superabsorbent may be deposited on the carrier web to form the superabsorbent layers. The superabsorbent layers may comprise AGM particles or AGM fibers. In general, such AGM's have been used only for their fluid-absorbing properties. Such materials form hydrogels on contact with liquid (e.g., with urine, blood, and the like). One highly preferred type of hydrogel-forming, absorbent gelling material is based on the hydrolyzed polyacids, especially neutralized polyacrylic acid. Hydrogel-forming polymeric materials of this type are those which, upon contact with fluids (i.e., liquids) such as water or body fluids, imbibe such fluids and thereby form hydrogels. In this manner, fluid discharged into the fluid absorbent structures herein can be acquired and held. These preferred superabsorbent polymers will generally comprise substantially water-insoluble, slightly cross-linked, partially neutralized, hydrogel-forming polymer materials prepared from polymerizable, unsaturated, acid-containing monomers.

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Fluid absorbent gelling material particles preferably have a particle size of from about 30 microns to about 2 mm for substantially all of the particles. "Particle Size" as used herein means the weighted average of the smallest dimension of the individual particles.

In some forms, the absorbent cores or portions thereof of the present disclosure may be substantially free of airfelt and are thus distinct from mixed layers that may include airfelt. As used herein, "substantially free of airfelt" means less than 5%, 3%, 1%, or even 0.5% of airfelt. In some forms, there may be no measurable airfelt in the superabsorbent layers. In the case of the first superabsorbent layer, it is preferably disposed onto the first distribution layer discontinuously. And as noted previously, the second superabsorbent layer may, in conjunction with the first superabsorbent layer or independently thereof, be disposed on the second distribution layer discontinuously. As used herein "discontinuously" or "in a discontinuous pattern" means that the superabsorbent polymers are applied onto the first distribution layer in a pattern of disconnected shaped areas. These areas of superabsorbent polymers or areas free of superabsorbent polymer may include, but are not limited to linear strips, non-linear strips, circles, rectangles, triangles, waves, mesh, and combinations thereof. The first superabsorbent layer like the second superabsorbent layer may, however, be disposed onto its respective distribution layer in a continuous pattern. As used herein "continuous pattern" or "continuously" means that the material is deposited and or secured to a superabsorbent carrier material and/or the adjacent distribution layer in an uninterrupted manner such that there is rather full coverage of the distribution layer by the superabsorbent polymer.

In certain embodiments, the first and second superabsorbent layers may comprise superabsorbent polymers that are the same. In other embodiments, the first and second superabsorbent layers may comprise superabsorbent polymers that are different from one another. This is may be in addition to the different deposition patterns that are discussed above.

The superabsorbent layers are disposed having a thickness of 0.2 mm, 0.3 mm, 0.4 mm, or 0.5 mm to 1 mm, 1.2 mm, 1.4 mm, 1.8 mm, or 2 mm. The first and second superabsorbent layers may have the same or different cross-direction widths as applied to their respective distribution layers. For instance, the cross-direction widths of the first and second superabsorbent layers may be from 20 mm, 25 mm, 30 mm, 35 mm, or 40 mm to 50 mm, 60 mm, 65 mm, 70 mm, 80 mm, or 90 mm. Alternatively, in embodiments where the widths of the first and second superabsorbent layers differ from one another in the cross-direction width, the first superabsorbent layer may have a lesser cross-direction width than the second superabsorbent layer. In particular, the first superabsorbent layer may have a cross-direction width that is less than about 95%, 90%, 80%, 70%, or even 60% of the width of the second superabsorbent layer.

In certain embodiments, the one or both of the first and second superabsorbent layers span greater than greater than about 50%, 60%, 70%, 80%, 90%, or even 95% of the cross-direction width of a superabsorbent carrier layer and/or the respective adjoining first or second distribution layer.

Carrier Webs/Optional Layers

Recall that carrier webs may comprise the primary topsheet and/or the secondary topsheet. And, like the optional layers that may be included in the chassis, the absorbent system may also comprise similar optional layers. The following descriptions and attributes of the optional layers are also suitable for use in the carrier web. For the sake of facility, the term "webs" shall encompass the optional layer web as well as carrier webs. The optional layers and/or carrier webs may be webs selected from the group consisting of a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

These optional layers and/or carrier webs may comprise materials such as creped cellulose wadding, fluffed cellulose fibers, airfelt, and textile fibers. The materials of the webs may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The optional layers may be any combination of the materials listed above and/or a plurality of the materials listed above, alone or in combination. The materials of the webs may be hydrophobic or hydrophilic depending on their placement within the chassis.

The materials of the webs may comprise constituent fibers comprising polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a superabsorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e., capillary and round) and the like. The constituent fibers may range from about 0.1 denier to about 100 denier.

The webs may include thermoplastic particulates or fibers. The materials, and in particular thermoplastic fibers, may be made from a variety of thermoplastic polymers including polyolefins such as polyethylene (e.g., PULPEX™) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse™ by Glyco Chemical, Inc. of Greenwich, Conn. Besides nonionic surfactants, anionic surfactants may also be used. These surfactants may be applied to the thermoplastic fibers at levels of, for example, from about 0.2 to about 1 $g/cm^2$ of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the webs of this disclosure may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON™, CEL-BOND™, or CHISSO™ bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e., unbent) or crimped (i.e., bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The webs may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON™, and KODEL™), high melting crimped polyester fibers (e.g., KODEL™ 431 made by Eastman Chemical Co.) hydrophilic nylon (HYDRO-FIL™), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

Distribution Layers

The first and second distribution layers are useful for wicking bodily fluids away from the skin of a wearer to facilitate comfort of continued wear after a release. In some forms, the support web may comprise the distribution layer. In some forms, the support web may be configured similar to the carrier web described herein. In some forms, the first and second distribution layers of the first and/or second laminates not only face one another but are joined in an offset manner to form part of the core. The distribution layers comprise one or more of cellulose and commuted wood pulp. This may be in the form of airlaid. The airlaid may be chemically or thermally bonded. In particular, the airlaid may be multi bonded airlaid (MBAL). In this instance, the distribution layer may further comprise a fibrous thermoplastic adhesive material at least partially bonding the airlaid to itself and adjacent distribution layers, superabsorbent layers, or other additional (optional) layers. It should be noted that the same materials that are suitable for the optional layers of the chassis are envisioned as suitable for use in the distribution layers. The basis weight for each of the first and second distribution layers range from 80 gsm, 80 gsm, 100 gsm, 110 gsm, 120 gsm, or 130 gsm to 140 gsm, 150 gsm, 160 gsm, 180 gsm, 200 gsm, 220 gsm, or 240 gsm. A preferred basis weight is 135 gsm for each of the distribution layers of the first and second laminates. The support web 870 (shown in FIGS. 8. 10, 11, and 13) may comprise the same makeup as the distribution layer.

Health Benefit Agents

As noted previously, in some forms, health benefit agents may be deposited on the carrier webs described herein. Some suitable health benefit agents include prebiotics, e.g. oligofructose, clay, e.g. laponite, activated charcoal, carbon, organic acids, e.g. lactic acid, xylitol, and/or antioxidants, e.g. vitamin C. In some forms, combinations of such actives may be provided on the carrier web or in other portions of the absorbent article, e.g. topsheet, barrier cuffs, secondary topsheet, distribution layers, or any combination thereof. Health benefit agents are disclosed in additional detail in U.S. Pat. No. 8,552,251.

Barrier Cuffs

Referring back to FIG. 2, the incontinence pad 10 may further comprise a first barrier cuff 230A and a second barrier cuff 230B and fastening adhesive 211 disposed on the garment-facing surface 20B of the chassis 20. As shown, the fastening adhesive 211 may not extend out laterally to the same extent as the absorbent system 205. As such, constructions where pad curl is reduced would be beneficial.

The first barrier cuff 230A and the second barrier cuff 230B may be attached to the chassis 20 in any suitable location. For example, as shown, the first barrier cuff 230A and the second barrier cuff 230B may be attached to a wearer-facing surface 20A of the chassis 20. As shown, the first barrier cuff 230A and the second barrier cuff 230B are attached to the primary topsheet 203. In some forms, the first barrier cuff 230A and the second barrier cuff 230B may be attached to a garment-facing surface 20B of the chassis 20. For example, the first barrier cuff 230A and the second barrier cuff 230B may be attached to the backsheet 207. Some examples of other suitable barrier cuffs are described in U.S. Pat. Nos. 4,695,278; 4,704,115; 4,795,454; 4,909, 803; U.S. Patent Application Publication No. 2009/0312730.

As shown, in some forms, the first barrier cuff 230A comprises a first cover 231 and a first elastic member 233. The second barrier cuff 230B comprises a second cover 235 and a second elastic member 237. As shown, the first cover 231 may fully enclose the first elastic member 233. Similarly, the second cover 235 may fully enclose the second elastic member 237.

While the first barrier cuff 230A and the second barrier cuff 230B are shown as discrete elements which are attached to the chassis 20, any suitable configuration may be utilized. For example, the first cover 231 and/or the second cover 235 may comprise a portion of the primary topsheet 203 and/or a portion of the backsheet 207. In such forms, the first barrier cuff 230A and/or the second barrier cuff 230B may be integrally formed with the chassis 20. A form where the first barrier cuff 230A and the second barrier cuff 230B are integrally formed with the chassis 20 is shown in FIG. 2 and discussed hereafter.

The first elastic member 233 and the second elastic member 237 may be attached to the first cover 231 and the second cover 235, respectively, by any suitable means. In one example, the first elastic member may be adhesively attached to the first cover 231. Similarly, the second elastic member 237 may be adhesively attached to the second cover 235. For example, as shown, first adhesive portions 251 and 253 may attach the elastic members 233 and 237 to their respective covers 231 and 235. Similarly, second adhesive portions 255 and 257 may attach their respective covers 231 and 235 to the primary topsheet 203. As described below, the first elastic member 233 and the second elastic member 237 may be attached in only a portion the first cover 231 and second cover 235, respectively. Additional forms are contemplated where the first elastic member 233 and/or the second elastic member 237 are attached to the chassis 20 in conjunction with or independently from their respective covers 231 and 235.

As shown, the elastic members 233 and 237 may be disposed laterally inboard of side edges 205A and 205B of the absorbent system 205. In other forms, the elastic members 233 and 237 may be disposed laterally outboard of the side edges 205A and 205B of the absorbent system 205. Still in other forms, the elastic members 233 and 237 may be disposed laterally inboard of the side edges 205A and 205B of the absorbent system 205 in the first end region 40 and the second end region 48 but laterally outboard of side edges 205A and 205B of the absorbent system 205 in the intermediate region 44. Additional forms are contemplated where the elastic members 233 and 237 are disposed laterally inboard of the side edges 205A and 205B of the absorbent system 205 in the first end region 40 but are disposed outboard of the side edges 205A and 205B of the absorbent system 205 in the intermediate region 44 and/or the second end region 48.

The elastic members comprised by the barrier cuffs can be glued in, in various glue lengths using various glues and glue amounts and placements. Placement of the glue is yet another variable which should be considered especially when designed with the core flexibility in mind. Gluing of the elastic members and the covers create anchor points on the pad.

The covers of the barrier cuffs of the present invention can be made of varying types of nonwovens of different MD and CD flexibility. The cover can be bonded to the topsheet of the absorbent article, such as, for example, by a slot coated stripe of adhesive, glue beads, ultrasonic sealing, or other suitable bonding agents. In certain forms of the present invention, the cover can be bonded to the backsheet at the side edges 22 and 24 (see FIG. 1) of the pad, such as, for example, using a crimp or other suitable bonding agents, such as, for example, adhesive.

Elastic members may comprise any suitable elastic material. Some suitable examples include Spandex™ or other similar polyurethanes, natural or synthetic rubber, styrene block copolymers, metallocene polyolefins, Lycra™, or any other suitable elastomer materials known in the art. Preferably the elastic member is durable for ease of processing and for during the use of the article and exhibits excellent elasticity (recovery after strain) even under strains as high as 400%.

Additionally, the elastic members of the present disclosure may comprise any suitable dtex. In other forms, the elastic members may comprise a dtex of 680 or less. In some forms, the elastic members may have a dtex between 680 and 470, specifically including all numbers within the range and any ranges created thereby.

Minimum spacing between the first barrier cuff 230A and the second barrier cuff 230B may be largely driven by female anatomy. However, tradeoffs can occur where the barrier cuffs (and their respective elastic members) are disposed too far outboard of the absorbent system 205 and too far inboard of the absorbent system 205. As such, spacing between the most distal elastic members of their respective barrier cuffs should be carefully selected. Starting from the narrowest width, spacing between the most distal elastic members of the first barrier cuff 230A and the second barrier cuff 230B should be large enough to allow sufficient access to the absorbent system 205 during use while also taking into account the forces which will be applied to the pad. If too narrow, access to a portion of the absorbent system 205 could be obstructed which could lead to leakage despite the barrier cuffs 230A and 230B. In some forms of the present invention, minimum spacing between the elastic member of the first barrier cuff 230A and the elastic member of the second barrier cuff 230B which are most distal to one another may be at least 20 mm. Any suitable spacing may be utilized. For example, in some forms of the present invention, the spacing may be greater than or equal to about 20 mm, greater than about 30 mm, greater than about 33 mm, greater than about 35 mm, greater than about 40 mm, greater than about 45 mm, greater than about 50 mm, greater than about 54 mm, greater than about 60 mm, greater than about 65 mm, less than or equal to about 70 mm, or less than about 65 mm, or less than about 60 mm, less than about 55 mm, less than about 50 mm, less than about 45 mm, less than about 40 mm, less than about 35 mm, less than about 30 mm, less than about 25 mm, specifically including any values within these ranges or any ranges created thereby.

Test Methods

Linear Distances

Linear distances may be measured by any appropriate instrument that is calibrated and capable of a measurement to the nearest 0.1 mm.

Basis Weight Test

A 9.00 cm$^2$ large piece of sample substrate, i.e., 1.0 cm wide by 9.0 cm long, is used. The sample may be cut out of a consumer product, such an absorbent article. The sample needs to be dry and free from other materials like glue or dust. Samples are conditioned at 23° Celsius (±2° C.) and at a relative humidity of about 50% (±5%) for 2 hours to reach equilibrium. The weight of the cut nonwoven substrate is measured on a scale with accuracy to 0.0001 g. The resulting mass is divided by the specimen area to give a result in g/m$^2$ (gsm). Repeat the same procedure for at least 20 specimens from 20 identical consumer products or packaging materials therefor. If the consumer product or packaging materials therefor are large enough, more than one specimen can be obtained from each. An example of a sample is a portion of a topsheet of an absorbent article. If the local basis weight variation test is done, those same samples and data are used for calculating and reporting the average basis weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making an absorbent article comprising the steps of:

obtaining a carrier web and transporting the carrier web in a machine direction;

obtaining a first absorbent core web and a second absorbent core web;

serially cutting the first absorbent core web thereby forming a plurality of discrete first absorbent cores each having a first core first cut edge and a first core second cut edge;

serially cutting the second absorbent core web thereby forming a plurality of discrete second absorbent cores each having a second core first cut edge and a second core second cut edge;

arranging a discrete first absorbent core and a discrete second absorbent core in a longitudinally offset configuration, wherein the first core first cut edge extends longitudinally outboard of one of the second core first cut edge and second core second cut edge, and the other of the second core first cut edge and second core second cut edge extends longitudinally outboard of the first core second cut edge;

applying a first deposit of adhesive between the discrete first absorbent core and the discrete second absorbent core, whereby at least a portion of the first deposit of adhesive will contact the carrier web between the carrier web and the discrete second absorbent core longitudinally outboard of the discrete first absorbent core and wherein the first deposit of adhesive does not extend longitudinally beyond the second core first cut edge or second core second cut edge;

joining the first absorbent core to the second absorbent core and to the carrier web in the offset configuration, thereby forming a laminate structure web;

joining a backsheet web to the laminate structure web thereby forming an absorbent article web; and cutting the absorbent article web into a plurality of discrete absorbent articles.

2. The method of claim 1 wherein the respective first and second cut edges of either or both the first discrete absorbent cores and the second discrete absorbent cores have non-linear cut profiles.

3. The method of claim 2 wherein the non-linear cut profiles are matching and nested.

4. The method of claim 1, wherein the carrier web comprises a topsheet web or a combination of a topsheet and secondary topsheet.

5. The method of claim 1, wherein the carrier web comprises a secondary topsheet web.

6. The method of claim 1, wherein the discrete first absorbent cores have a first width and the discrete second absorbent cores have a second width, and wherein the first width is less than the second width.

7. The method of claim 1, further comprising the steps of obtaining an absorbent core web and slitting the absorbent core web to form the first absorbent core web and the second absorbent core web.

8. The method of claim 1, wherein the step of cutting the first absorbent core web provides the discrete first absorbent cores with a first leading edge and a first trailing edge and the step of cutting the second absorbent core web provides the discrete second absorbent cores with a second leading edge and a second trailing edge, wherein at least one of the first leading edge or first trailing edge is convex and the other is concave, and wherein at least one of the second leading edge or the second trailing edge is convex and the other is concave.

* * * * *